United States Patent
Kirchgesser et al.

(10) Patent No.: US 7,329,491 B2
(45) Date of Patent: Feb. 12, 2008

(54) METHODS FOR ISOLATING NUCLEIC ACIDS

(75) Inventors: Michael Kirchgesser, Taufkirchen (DE); Frank Bergmann, Iffeldorf (DE); Thomas Walter, Penzberg (DE); Kurt Weindel, Wielenbach-Hardt (DE); Ralf Zielenski, Benediktbeuern (DE); Emad Sarofim, Hagendorn (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 300 days.

(21) Appl. No.: 10/962,916

(22) Filed: Oct. 12, 2004

(65) Prior Publication Data
US 2005/0079535 A1    Apr. 14, 2005

(30) Foreign Application Priority Data
Oct. 13, 2003  (EP) ................................. 03023039
Jul. 28, 2004  (EP) ................................. 04017856

(51) Int. Cl.
*C12Q 1/68*   (2006.01)
*C07H 21/00*  (2006.01)
*C07H 21/02*  (2006.01)
*C07H 21/04*  (2006.01)

(52) U.S. Cl. ..................... 435/6; 536/25.3; 536/23.1; 536/24.3

(58) Field of Classification Search ................. 435/6; 536/25.4, 23.1, 24.3
See application file for complete search history.

(56) References Cited

U.S. PATENT DOCUMENTS

| | | | |
|---|---|---|---|
| 4,683,195 | A | 7/1987 | Mullis et al. |
| 5,124,444 | A | 6/1992 | Van Ness et al. |
| 5,130,238 | A | 7/1992 | Malek et al. |
| 5,210,015 | A | 5/1993 | Gelfand et al. |
| 5,340,776 | A * | 8/1994 | Paschke et al. ............... 501/11 |
| 5,487,972 | A | 1/1996 | Gelfand et al. |
| 5,804,375 | A | 9/1998 | Gelfand et al. |
| 5,804,684 | A | 9/1998 | Su |
| 6,037,465 | A | 3/2000 | Hillebrand et al. |
| 6,383,393 | B1 * | 5/2002 | Colpan et al. ............... 210/656 |
| 2001/0041332 | A1 | 11/2001 | Hillebrand et al. |
| 2003/0143566 | A1 * | 7/2003 | Helftenbein ................... 435/6 |
| 2003/0175988 | A1 * | 9/2003 | Yarmoluk et al. ........... 436/172 |
| 2005/0266462 | A1 * | 12/2005 | Weindel et al. ................. 435/6 |

FOREIGN PATENT DOCUMENTS

| | | |
|---|---|---|
| EP | 0439182 A2 | 7/1991 |
| EP | 0512767 A1 | 11/1992 |
| EP | 0658164 B1 | 6/1995 |
| EP | 0757106 A2 | 2/1997 |
| WO | WO 90/01069 | 2/1990 |
| WO | WO 91/00212 | 1/1991 |
| WO | WO 92/02638 | 2/1992 |
| WO | WO 95/01359 | 1/1995 |
| WO | 97/08547 A1 | 3/1997 |
| WO | WO 99/16781 | 4/1999 |
| WO | 00/34463 A1 | 6/2000 |
| WO | WO 01/37291 A1 | 5/2001 |
| WO | WO 02/08800 A2 | 1/2002 |

OTHER PUBLICATIONS

The Stratagene Catalog p. 39 (1988).*
Alderton, R. et al., "Magnetic Bead Purification of M13 DNA Sequencing Templates," Analytical Biochemistry 201, 166-169 (1992).
Barney, F., "Genetic disease detection and DNA amplification using cloned thermostable ligase," Proc. Natl. Acad. Sci. USA, vol. 88, pp. 189-193, Jan. 1991.
Barney, F., "The Ligase Chain Reaction in a PCR World," PCR Methods and Applications, 1:5-16, 1991.
Boom, R. et al., "Rapid and Simple Method for Purification of Nucleic Acids," Journal of Clinical Microbiology, Mar. 1990, pp. 495-503.
Guatelli, John C. et al., "Isothermal, in vitro amplification of nucleic acids by a multienzyme reaction modeled after retroviral replication," Proc. Natl. Acad. Sci., USA, vol. 87, pp. 1874-1878, Mar. 1990.
Jakobi, R. et al., "Filter-Supported Preparation of λ Phage DNA," Analytical Biochemistry 175, 196/201 (1988).
Marko, M.A. et al., "A Procedure for the Large-Scale Isolation of Highly Purified Plasmid DNA Using Alkaline Extraction and Binding to Glass Powder," Analytical Bichemistry, 121, 382-387 (1982).
Vogelstein, B. et al., "Preparative and analytical purification of DNA from agarose," Proc. Natl. Acad. Sci. USA, col. 76, No. 2, pp. 615-619, Feb. 1979.
Whelen, A. et al., "The Role of Nucleic Acid Amplification and Detection in the Clinical Microbiology Laboratory," Auun. Rev. Microbiol. 1996, 50: 349-373.

(Continued)

*Primary Examiner*—Ethan Whisenant
(74) *Attorney, Agent, or Firm*—Marilyn L. Amick; Roche Diagnostics Operations, Inc.

(57) ABSTRACT

A method for purification of a nucleic acid comprising the steps of (a) adsorbing on a substrate the nucleic acid from a composition containing (i) an aqueous buffer, (ii) salts in a high concentration, (iii) a water-miscible, non-acidic organic compound, and (iv) the nucleic acid; (b) optionally washing with a washing solution the substrate with the adsorbed nucleic acid; (c) contacting the substrate with the adsorbed nucleic acid with a solution containing salts in a lower concentration compared to the composition of step (a), thereby desorbing the nucleic acid from the substrate; (d) separating the solution with the desorbed nucleic acid from the substrate, thereby purifying the nucleic acid; and optionally (e) precipitating the desorbed nucleic acid from the solution of step (d) and isolating the precipitated nucleic acid, thereby further purifying the nucleic acid.

32 Claims, 5 Drawing Sheets

OTHER PUBLICATIONS

Wu, D. Y. et al., "The Ligation Amplification Reaction (LAR)—Amplification of Specific DNA Sequences Using Sequential Rounds of Template-Dependent Ligation," Genomics 4, 560-569 (1989).

Yamada, O. et al., "A new method for extracting DNA or RNA for polymerase chain reaction," Journal of Virological Methods, 27 (1990) 203-210.

Ausubel, et al., *Current Protocols in Molecular Biology, J. Wiley and Sons*, NY 1987.

Sambrook, Fritsch & Maniatis, *Molecular Cloning, A Laboratory Manual*, 3$^{rd}$ *Edition*, CSHL Press 2001.

* cited by examiner

METHODS FOR ISOLATING NUCLEIC ACIDS

RELATED APPLICATIONS

This application claims priority to European patent applications EP 03023039.5 filed Oct. 13, 2003 and EP 04017856.8 filed Jul. 28, 2004.

FIELD OF THE INVENTION

The present invention is directed to the purification of a nucleic acid. Particularly, the invention is directed to methods of adsorbing a nucleic acid present in an aqueous adsorption solution to a solid substrate.

BACKGROUND OF THE INVENTION

Many biological substances, especially nucleic acids, present special challenges in terms of isolating them from their natural environment. On the one hand, they are often present in very small concentrations and, on the other hand, they are often found in the presence of many other solid and dissolved substances, e.g., after lysis of cells. This makes them difficult to isolate or to measure, in particular in biospecific assays which allow the detection of specific nucleic acids or the detection of specific properties of a nucleic acid. Such biospecific assays play a major role in the field of diagnostics and bioanalytics in research and development. Examples of biospecific assays are hybridization assays, immunoassays, and receptor-ligand assays. Hybridization assays use specific base-pairing for the molecular detection of nucleic acid analytes, e.g., RNA and DNA. Hence, oligonucleotide probes with a length of 18 to 20 nucleotides may enable the specific recognition of a selected complementary sequence, e.g., in the human genome. Another assay which entails the selective binding of two oligonucleotide primers is the polymerase chain reaction (PCR) described in U.S. Pat. No. 4,683,195. This method allows the selective amplification of a specific nucleic acid region to detectable levels by a thermostable polymerase in the presence of deoxynucleotide triphosphates in several cycles.

As described above, before nucleic acids may be analyzed in one of the above-mentioned assays or used for other processes, they have to be isolated or purified from biological samples containing complex mixtures of different components such as, e.g., proteinaceous and non-proteinaceous components. Often, for the first steps, processes are used which allow the enrichment of the component of interest, i.e., the nucleic acids. Frequently, these are contained in a bacterial cell, a fungal cell, a viral particle, or the cell of a more complex organism, such as a human blood cell or a plant cell. Nucleic acids as a component of interest can also be called a "target component".

To release the contents of said cells or particles, they may be treated with enzymes or with chemicals to dissolve, degrade, or denature the cellular walls and cellular membranes of such organisms. This process is commonly referred to as lysis. The resulting solution containing such lysed material is referred to as a lysate. A problem often encountered during the lysis is that other enzymes degrading the target component, e.g., deoxyribonucleases or ribonucleases degrading nucleic acids, come into contact with the target component during lysis. These degrading enzymes may also be present outside the cells or may have been spatially separated in different cellular compartments before the lysis and come now into contact with the target component. Other components released during this process may be, e.g., endotoxins belonging to the family of lipopolysaccharides which are toxic to cells and can cause problems for products intended to be used in human or animal therapy.

In the next steps of the sample preparation which follow on the lysis step, the nucleic acids are further enriched. Nucleic acids are normally extracted from the complex lysis mixtures before they are used in a probe-based assay. There are several methods for the extraction of nucleic acids. Sequence-dependent or biospecific methods include, e.g., affinity chromatography or hybridization to immobilized probes. Sequence-independent or physico-chemical methods include, e.g., liquid-liquid extraction with phenol-chloroform, precipitation with pure ethanol or isopropanol, extraction with filter paper, extraction with micelle-forming agents as cetyl trimethyl ammonium bromide, binding to immobilized, intercalating dyes such as acridine derivatives, adsorption to substrates such as silica gel or diatomic earths, and adsorption to magnetically attractable glass particles or organo silane particles under chaotropic conditions. Direct binding of the nucleic acids to a substrate such as a material with a silica surface is preferred because among other reasons the nucleic acids do not have to be modified, and even native nucleic acids can be bound.

Particularly interesting for extraction purposes is the adsorption of nucleic acids to a glass surface, although other surfaces are possible.

Many procedures for isolating nucleic acids from their natural environment have been proposed in recent years by the use of their binding behavior to substrates such as glass surfaces. It is common to use chaotropic agents such as, e.g., guanidine thiocyanate or anionic, cationic, zwitterionic, or non-ionic detergents when nucleic acids are intended to be set free. It is also an advantage to use proteases, which rapidly degrade these enzymes or unwanted proteins. Nucleic acids which are set free, e.g., after cell lysis and/or lysis of cellular organelles such as mitochondria, plastids, nuclei, or other nucleic acid-containing organelles, can be purified by way of binding to a substrate such as a mineral support, washing said mineral support with the bound nucleic acids, and releasing, i.e., desorbing said nucleic acids from said mineral support. For a washing step, conditions are chosen by the skilled artisan under which the nucleic acids remain adsorbed to the mineral support. Typically, greater than 40%, more typically greater than 50%, more typically greater than 70%, more typically greater than 80%, even more typically greater than 90%, even more typically greater than 95%, even more typically greater than 99% of the nucleic acids remain adsorbed to the mineral support. For the desorbing step, conditions are chosen by the skilled artisan under which the nucleic acids are released from the mineral support. Typically, greater than 40%, more typically greater than 50%, more typically greater than 70%, more typically greater than 80%, even more typically greater than 90%, even more typically greater than 95%, even more typically greater than 99% of the nucleic acids are released from the mineral support.

Adsorption of nucleic acids to glass particles or silica particles in the presence of chaotropic salts is known to the art (Vogelstein, B., and Gillespie, D., Proc. Natl. Acad. Sci. USA 76 (1979) 615-619) and provides the basis for chromatographic purification and separation processes for nucleic acids. Also known to the art are methods to isolate and purify RNA and DNA from lysates using high concentrations of chaotropic salts, e.g., sodium iodide, sodium perchlorate, and guanidine thiocyanate (Boom, R., et al., J.

Clin. Microbiol. 28 (1990) 495-503; Yamada, O., et al., J. Virol. Methods 27 (1990) 203-209). The purification of plasmid DNA from bacteria on glass dust in the presence of sodium perchlorate is described in Marko, M. A., et al., Anal. Biochem. 121 (1982) 382-387. In DE 37 24 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing tris/EDTA buffer. A similar procedure for purifying DNA from lambda phages is described in Jakobi, R., et al., Anal. Biochem. 175 (1988) 196-201. The procedure entails the selective binding of nucleic acids to glass surfaces in chaotropic salt solutions and separating the nucleic acids from contaminants such as agarose, proteins, or cell residue. To separate the glass particles from the contaminants, the particles may be either centrifuged or fluids are drawn through glass fiber filters. This is a limiting step, however, that prevents the procedure from being used to process large quantities of samples.

The use of magnetic particles to immobilize nucleic acids after precipitation by adding salt and ethanol is more advantageous and is described, e.g., in Alderton, R. P., et al., Anal. Biochem. 201 (1992) 166-169 and WO 91/00212. In this procedure, the nucleic acids are agglutinated along with the magnetic particles. The agglutinate is separated from the original solvent by applying a magnetic field and performing a wash step. After one wash step, the nucleic acids are dissolved in a tris buffer. This procedure has a disadvantage, however, in that the precipitation is not selective for nucleic acids. Rather, a variety of solid and dissolved substances are agglutinated as well. As a result, this procedure can not be used to remove significant quantities of any inhibitors of specific enzymatic reactions that may be present. Magnetic porous glass is also available on the market that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin. Magnetizable particular adsorbents proved to be very efficient and suitable for automatic sample preparation. Ferrimagnetic and ferromagnetic as well as superparamagnetic pigments are used for this purpose. The most typical magnetic glass particles are those described in WO 01/37291.

Purification of a nucleic acid by way of adsorbing the same to a substrate such as a mineral substrate in the presence of high concentration of salts is also applied to other complex mixtures. Examples therefor are known to the person skilled in the art of molecular biology and include reaction mixtures following, e.g., in vitro synthesis of nucleic acids such as PCR, restriction enzyme digestions, ligation reactions, etc.. In Vogelstein, B., and Gillespie, D., Proc. Natl. Acad. Sci. USA 76 (1979) 615-619, for instance, a procedure for binding nucleic acids from agarose gels in the presence of sodium iodide to ground flint glass is proposed. Another application for purification of a nucleic acid by way of adsorbing the same to a substrate such as a mineral substrate in the presence of a high concentration of salts is the removal of pyrogenic contaminants which may have copurified with the nucleic acid.

The mechanism by which nucleic acids bind to the mineral support in the presence of chaotropic agents is not entirely clear. It is hypothesized that the interaction between the nucleic acids and the solvent is influenced such that the nucleic acids adsorb to the mineral support and denaturant. In the presence of high concentrations of chaotropic agents the reaction is almost quantitative. The adsorbed nucleic acids can be eluted by applying to the mineral support buffers of low ionic strength.

EP 0 658 164 describes a method for the chromatographic purification of nucleic acids by way of chromatographic purification. Nucleic acids are adsorbed to a substrate, i.e., a mineral support, from an aqueous adsorption solution with a high salt concentration which typically contains a chaotropic agent. The aqueous adsorption solution comprises 1%-50% of aliphatic alcohol with a chain length of C1-C5 and/or polyethylene glycol and/or hydrophobic inorganic and/or organic polymers and/or organic acid such as trichloroacetic acid.

The methods for the isolation/purification of nucleic acids of the state of the art have certain disadvantages. Such disadvantages relate to, e.g., purity, selectivity, recovery rate, laboratory safety, and convenience, as well as to the speed of the isolation/purification process. For example, in protocols using a phenol/chloroform extraction, residual phenol is often a problem for certain post isolation procedures, particularly for enzymatic reactions such as a digestion with a restriction enzyme, the polymerase chain reaction (PCR), or a ligase-mediated reaction. Generally, elevated concentrations of residual reagents from the purification/isolation process may pose a problem. It is therefore desired to keep residual amounts of the reagents used during the purification procedure as low as possible in the purified nucleic acid. Another potential problem related to purity is the coextraction of certain substances from the adsorption matrix (leaching). It is therefore desired to keep residual amounts of compounds liberated during the purification procedure by leaching as low as possible in the purified nucleic acid.

Another disadvantage of state of the art protocols which use ethanol or isopropanol in the adsorption solution is the high volatility and flammability of such alcohols. On the one hand, these flammable alcohols are potential hazards in laboratory practice. Also, depending on national regulations, flammable alcohols may pose logistical problems with regard to allowable storage and transport. In addition, volatile alcohols are difficult to dose with precision because of their vapor pressure. It is therefore desired to replace flammable alcohols by substances which are less hazardous or/and which pose fewer logistical problems.

Exemplary kits which are commercially available for sample preparation of nucleic acids are the High Pure product line (Roche Diagnostics GmbH, Mannheim, Germany). The adsorption solution is transferred to a High Pure column and passed through a fleece containing glass fiber material. During this process the nucleic acids are adsorbed to the glass material. When using the columns of the Roche High Pure kit and a protocol for nucleic acid isolation/purification from serum making use of ethanol in the adsorption solution, it was noted that high triglyceride concentrations in serum lead to a prolonged time needed to pass the adsorption solution through the glass fiber fleece (also see Example 6). It is therefore desired to identify a substitute for ethanol which, considering sample preparation from serum with high triglyceride concentrations, reduces the time needed to pass the adsorption solution through the glass fiber fleece.

The problem underlying the present invention is therefore to provide an alternative method for the purification of a nucleic acid using alternative substances in the aqueous adsorption solution in order to facilitate the binding of a nucleic acid to a substrate such as a mineral support.

SUMMARY OF THE INVENTION

Surprisingly, it has been found that a nucleic acid can be bound to a substrate if the adsorption solution of high ionic strength contains a water-miscible, non-acidic organic compound comprising a functional group of the formula $$W= \!\!=\!\!= Z$$

whereby W is a carbon atom or a sulfur atom and Z is an oxygen atom or a nitrogen atom.

Thus, of the invention, in a first embodiment a method is provided for the purification of a nucleic acid, comprising the steps of a) adsorbing on a substrate the nucleic acid from a composition containing (i) an aqueous buffer, (ii) salts in a high concentration, and (iii) a water-miscible, non-acidic organic compound comprising a functional group of the formula $$W= \!\!=\!\!= Z$$

whereby W is a carbon atom or a sulfur atom and Z is an oxygen atom or a nitrogen atom, and (iv) the nucleic acid; b) optionally washing with a washing solution the substrate with the adsorbed nucleic acid, followed by c) contacting the substrate with the adsorbed nucleic acid with a solution containing salts in a lower concentration compared to the composition of step (a), thereby desorbing the nucleic acid from the substrate, and d) separating the solution with the desorbed nucleic acid from the substrate, thereby purifying the nucleic acid, and optionally (e) precipitating the desorbed nucleic acid from the solution of step (d) and isolating the precipitated nucleic acid, thereby further purifying the nucleic acid.

Another embodiment of the invention is a method for adsorbing a nucleic acid on a substrate, comprising the steps of (a) providing the nucleic acid in an aqueous solution containing salts in a high concentration and a water-miscible, non-acidic organic compound comprising a functional group of the formula W====Z whereby W is a carbon atom or a sulfur atom and Z is an oxygen atom or a nitrogen atom; followed by (b) adding the aqueous solution of step (a) to the substrate.

Yet, another embodiment of the invention is a method for adsorbing a nucleic acid on a substrate, comprising the steps of (a) providing the nucleic acid in an aqueous solution containing salts in a high concentration; (b) providing the substrate in the form of powdered material; (c) providing a water-miscible, non-acidic organic compound comprising a functional group of the formula W====Z whereby W is a carbon atom or a sulfur atom and Z is an oxygen atom or a nitrogen atom; followed by dispersing the substrate of step (b) in the water-miscible, non-acidic organic compound of step (c) to form a suspension of said substrate; and (e) mixing the aqueous solution of step (a) with the suspension of step (d).

Yet, another embodiment of the invention is a suspension containing a substrate in the form of powdered material dispersed in a water-miscible, non-acidic organic compound comprising a functional group of the formula W====Z whereby W is a carbon atom or a sulfur atom and Z is an oxygen atom or a nitrogen atom.

Yet, another embodiment of the invention is the use of a water-miscible, non-acidic organic compound comprising a functional group of the formula W====Z whereby W is a carbon atom or a sulfur atom and Z is an oxygen atom or a nitrogen atom, for performing the methods of the invention described herein. Yet, another embodiment of the invention is the use of a water-miscible, non-acidic organic compound comprising a functional group of the formula W====Z whereby W is a carbon atom or a sulfur atom and Z is an oxygen atom or a nitrogen atom, for preparing a suspension by way of dispersing a substrate in said water-miscible, non-acidic organic compound to form a suspension of said substrate. Yet, another embodiment of the invention is the use of a suspension of the invention for performing a method of the invention.

Other embodiments of the invention are kits of parts containing a water-miscible, non-acidic organic compound comprising a functional group of the formula W====Z whereby W is a carbon atom or a sulfur atom and Z is an oxygen atom or a nitrogen atom.

It has also been found that that nucleic acids can be bound to a substrate if the adsorption solution of high ionic strength contains a water-miscible cyclic diether.

Thus, another embodiment of the invention is a method for the purification of a nucleic acid comprising the steps of a) adsorbing on a substrate the nucleic acid from a composition containing (i) an aqueous buffer, (ii) salts in a high concentration, (iii) a water-miscible cyclic diether, (iv) the nucleic acid; b) optionally washing with a washing solution the substrate with the adsorbed nucleic acid; followed by c) contacting the substrate with the adsorbed nucleic acid with a solution containing salts in a lower concentration compared to the composition of step (a), thereby desorbing the nucleic acid from the substrate; and (d) separating the solution with the desorbed nucleic acid from the substrate, thereby purifying the nucleic acid, and optionally (e) precipitating the desorbed nucleic acid from the solution of step (d) and isolating the precipitated nucleic acid, thereby further purifying the nucleic acid.

Yet, a further embodiment of the invention is a method for adsorbing a nucleic acid on a substrate, comprising the steps of (a) providing the nucleic acid in an aqueous solution containing salts in a high concentration and a water-miscible cyclic diether; and (b) adding the aqueous solution of step (a) to the substrate.

Yet, another embodiment of the invention is a method for adsorbing a nucleic acid on a substrate, comprising the steps of (a) providing the nucleic acid in an aqueous solution containing salts in a high concentration; (b) providing the substrate in the form of powdered material; (c) providing a water-miscible cyclic diether; (d) dispersing the substrate of step (b) in the water-miscible cyclic diether of step (c) to form a suspension of said substrate; and (e) mixing the aqueous solution of step (a) with the suspension of step (d).

Yet, another embodiment of the invention is a suspension containing a substrate in the form of powdered material dispersed in a water-miscible cyclic diether.

Yet, another embodiment of the invention is the use of a water-miscible cyclic diether, for performing the methods of the invention described herein. Yet, another embodiment of the invention is the use of a water-miscible cyclic diether, for preparing a suspension by way of dispersing a substrate in said water-miscible, non-acidic organic compound to form a suspension of said substrate. Yet, another embodiment of the invention is the use of a suspension of the invention for performing a method of the invention.

Other embodiments of the invention are kits of parts containing a water-miscible cyclic diether.

Another embodiment of the invention is a method for determining the presence of a nucleic acid in a biological sample, comprising the steps of (a) lysing the biological sample; (b) forming a composition containing (i) the lysed biological sample of step (a), (ii) an aqueous buffer, (iii) salts in a high concentration, (iv) a water-miscible, non-acidic organic compound comprising a functional group of the formula W═══Z whereby W is a carbon atom or a sulfur atom and Z is an oxygen atom or a nitrogen atom; (c) contacting the composition of step (b) with a substrate, thereby adsorbing the nucleic acid to the substrate; (d) optionally washing with a washing solution the substrate with the adsorbed nucleic acid; followed by (e) contacting the substrate with the adsorbed nucleic acid with a solution containing salts in a lower concentration compared to the composition of step (a), thereby desorbing the nucleic acid from the substrate; and (f) separating the solution with the desorbed nucleic acid from the substrate; and (g) detecting in the solution of step (f) the presence of the nucleic acid, thereby determining the presence of the nucleic acid. Typically, the nucleic acid is determined by amplification of the nucleic acid by means of the polymerase chain reaction using specific primers, a specific detection probe, and an amplification mixture, whereby amplification is monitored in real time.

Another embodiment of the invention is a method for determining the presence of a nucleic acid in a biological sample, comprising the steps of (a) lysing the biological sample; (b) forming a composition containing (i) the lysed biological sample of step (a), (ii) an aqueous buffer, (iii) salts in a high concentration, (iv) a water-miscible cyclic diether, whereby W is a carbon atom or a sulfur atom and Z is an oxygen atom or a nitrogen atom; (c) contacting the composition of step (b) with a substrate, thereby adsorbing the nucleic acid to the substrate; (d) optionally washing with a washing solution the substrate with the adsorbed nucleic acid; followed by (e) contacting the substrate with the adsorbed nucleic acid with a solution containing salts in a lower concentration compared to the composition of step (a), thereby desorbing the nucleic acid from the substrate; and (f) separating the solution with the desorbed nucleic acid from the substrate; and (g) detecting in the solution of step (f) the presence of the nucleic acid, thereby determining the presence of the nucleic acid.

DETAILED DESCRIPTION OF THE INVENTION

Figure 1A:
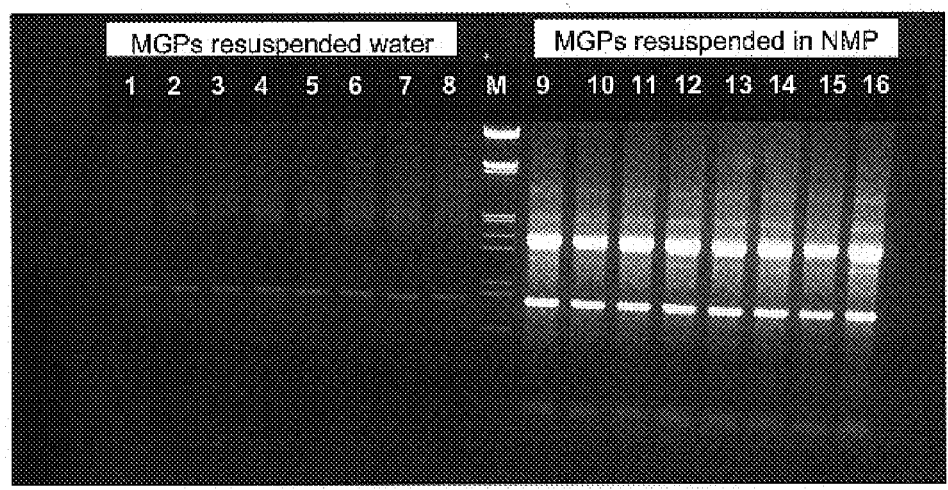
FIG. 1a: RNA was isolated from $10^6$ HeLa cells in 8-fold replicates using the respective protocol and kit of the MAG-NAPURE System (Roche Diagnostics GmbH, Mannheim). For these isolations, the magnetic glass particles were resuspended either in water or in N-methyl-2-pyrrolidone (NMP). The eluates with purified RNA were then analyzed on an agarose gel. The bands in lanes 1-8, i.e., RNA preparations using magnetic glass particles resuspended in water, are very weak and can hardly be reproduced. M indicates a size marker. Lanes 9-16 show RNA bands from preparations using magnetic glass particles resuspended NMP.

In the present document it is understood that the term "a nucleic acid" denotes at least one nucleic acid. Furthermore, the term "a nucleic acid" also may indicate a mixture of nucleic acids. The term "nucleic acid" encompasses RNA, DNA, or both. The term "substrate" denotes a substance which is substantially insoluble in an aqueous solution and on which a nucleic acid in an aqueous solution of high ionic strength can adsorb when the substance is added. Examples therefor are porous or non-porous mineral particles such as silica, glass, quartz, zeolites, or mixtures thereof. Also, the term "substrate" encompasses magnetically attractable particles coated with silica, glass, quartz, or zeolites. Further, it is understood that a substrate in the form of "powder" or "powdered" material refers to finely divided material which, when dispersed in a liquid phase such as a liquid organic compound or an aqueous solution, produces a suspension. The term "powder" or "powdered" material is intended to include tablets in which the powdered material has been aggregated but still yields a suspension when combined with the liquid organic compound or the aqueous solution. Further, it is understood that the terms "high ionic strength" and "high concentration" mean the ionic strength or concentration in an aqueous solution that results from dissolved salts in concentrations equal to or greater than about 1 M. Typical are salts present in the aqueous solution in concentrations of 1 to 10 M. More typical are chaotropic salts in concentrations of 1 to 8 M. Further, the term "water-miscible" indicates that at room temperature and normal atmospheric pressure the non-aqueous organic compound can be dissolved in water at a ratio equal or greater than 1% (percent) volume by volume, to form a homogeneous liquid phase. The term "non-acidic" organic compound denotes an organic compound lacking a carboxy function.

In detail, the procedure for binding a (at least one) nucleic acid (also referred to as target nucleic acid) to a substrate such as, e.g., glass particles can be described as follows. It is typically performed in the presence of chaotropic salts with a concentration of between 1 and 8 mol/l, and typically between 2 and 6 mol/l. Chaotropic salts can be sodium iodide, sodium perchlorate, guanidine thiocyanate, guanidine isothiocyanate or guanidine hydrochloride. Other substances such as lithium chloride, sodium chloride, potassium chloride, sodium acetate, urea, and mixtures thereof are also possible.

The purification effect results from the behavior of DNA or RNA to bind to material with a glass surface under these conditions, i.e., in the presence of certain concentrations of a chaotropic agent and, typically, a water-miscible, non-acidic organic compound. To bring the sample in contact with the substrate, i.e., the material with an affinity to nucleic acids, the sample is mixed with the material and incubated for a period of time sufficient for the binding to occur. Experts are usually familiar with the duration of the incubation step from procedures for performing treatment with non-magnetic particles. This step can be optimized by determining the quantity of immobilized biological material on the surface at different points in time. Incubation times of between 10 seconds and 30 minutes can be appropriate for nucleic acids. After incubation, the bound (at least one) target component, i.e., the nucleic acid(s) is separated from the liquid. This may be achieved in general by gravity or in the convenient case of nucleic acids bound to magnetic glass particles, by separating the material bound to the magnetic particles by applying a magnetic field. For instance, the magnetic particles can be pulled to the wall of the vessel in which incubation was performed. The liquid containing the sample contents that were not bound to the magnetic particles can then be removed. The removal procedure used depends on the type of vessel in which incubation was performed. Suitable steps include removing the liquid via pipetting or aspiration.

Another example is binding the nucleic acid in the adsorption solution to a glass fleece. Commercial kits often provide such a fleece at the bottom of a column. The adsorption solution containing the nucleic acid is transferred to the column and passed through the fleece by applying force. The term "force" includes gravitational force and, typically, centrifugal force. Very typical is the "spin column" procedure wherein the adsorption solution is passed through the filter due to force being applied by way of centrifugation. Other ways to pass the adsorption solution through the fleece include the application of pressure or suction.

The material with the bound DNA or RNA may then be washed at least once. Typically, the washing solution contains between more than 1 and less than 100 percent volume by volume of the water-miscible, non-acidic organic compound. Also typically, the washing solution contains between 1 and 100 percent volume by volume of the water-miscible, non-acidic organic compound. More typically, the washing solution is a mixture of 1-50% volume by volume of a water-miscible, non-acidic organic compound in water. Another very typical washing solution is a mixture of 40-80% volume by volume of a water-miscible, non-acidic organic compound with water. Another very typical washing solution is a mixture of 50-99% volume by volume of a water-miscible, non-acidic organic compound with water. Even more typical is a washing solution is a mixture of about 70% volume by volume of a water-miscible, non-acidic organic compound with water. Also typical for washing is the water-miscible, non-acidic organic compound, that is to say the pure liquid compound as obtained from commercial suppliers is also understood as being encompassed by the term "washing solution".

A wash solution is used that does not cause the (at least one) target nucleic acid(s) to be released from the material surface but that washes away the undesired contaminants as thoroughly as possible. This wash step typically takes place by incubating the material with the bound target nucleic acid(s) with the wash solution. The material is typically resuspended during this step. Also typically, in case the material is a glass fleece or a packing in a column, the washing step takes place by rinsing the column with the washing solution. Typically, the washing solution is passed through the column by applying pressure, suction, centrifugal force or gravitational force. The above equally applies when the water-miscible, non-acidic organic compound is used in pure form.

The contaminated wash solution is typically removed just as in the step described above for binding the nucleic acid to the substrate material. After the last washing step, the material can be dried briefly in a vacuum, or the fluid can be allowed to evaporate. A pretreatment step using acetone may also be performed.

Afterwards, the conditions may be reversed, e.g. the concentration of the chaotropic agent or the water-miscible, non-acidic organic compound is decreased to elute the DNA or RNA bound to the material. Typically, the process of separating the substrate, e.g. the magnetic glass particles, from the rest of the sample is done by pelleting the immobilized biological material, e.g. by gravity force or by the use of a magnet in the case of magnetic glass particles and removal of the supernatant. Then the magnetic glass particles with the immobilized biological material are resuspended in an aqueous solution with no or only a low amount of chaotropic agent and/or water-miscible, non-acidic organic compound. Alternatively, the suspension can be diluted with a solution with no or only a low amount of chaotropic agent and/ or water-miscible, non-acidic organic compound. Buffers of this nature are known from DE 37 24 442 and Jakobi, R., et al., Anal. Biochem. 175 (1988) 196-201. The elution buffers with a low salt content are in particular buffers with a content of less than 0.2 mol/l. Typically, the elution buffer contains the substance tris for buffering purposes. Also typically, the elution buffer is demineralized water. The solution containing purified DNA or RNA can now be used for other reactions. Optionally, the nucleic acid(s) can be precipitated from the solution using, e.g., ethanol or isopropanol. The precipitate can also be subjected to further washing steps. Methods of this kind are well known to the skilled artisan and are described in detail in Sambrook, Fritsch & Maniatis, Molecular Cloning, A Laboratory Manual, 3rd edition, CSHL Press, 2001.

For the adsorption and washing steps in the methods of the invention, typically liquids are used which are suitable for processes in molecular biology, in particular deoxyribonucleic acid (DNA) or ribonucleic acid (RNA) purification processes which make use of the binding of these substances to glass particles under certain conditions. Typical liquids comprise a water-miscible, non-acidic organic compound comprising a functional group of the formula $W\!=\!\!=\!\!Z$ whereby W is a carbon atom or a sulfur atom and Z is an oxygen atom or a nitrogen atom. Typically, the functional group is selected from the group consisting of an oxo group, a sulfoxo group, a cyano group, and a carbonyl group of a carbamoyl function or an amide but not belonging to a carboxy function. More typically, the water-miscible, non-acidic organic compound is selected from the group consisting of acetone, acetylacetone, acetonitrile, dimethylsulfoxide, diethylketone, methylethylketone, methylpropylketone, isobutylmethylketone, gamma-butyrolactone, gamma-valerolactone, propylene carbonate, and N-methyl-2-pyrrolidone. Also encompassed by the invention are liquids comprising as a water-miscible, non-acidic organic compound a cyclic diether. Typically, the cyclic diether is dioxane.

The magnetic glass particles used in the present invention may be provided in different formulations. It is possible to provide them in the form of a tablet, as a powder or as a suspension. Very typically, the magnetic glass particles are suspended in the water-miscible, non-acidic organic compound. Typically, these suspensions contain between 5 to 60 mg/ml magnetic glass particles. Also typically, the silica-containing material is suspended in aqueous buffered solutions which may optionally contain a chaotropic agent in a concentration of between 2 and 8 mol/l, and typically between 4 and 6 mol/l. Chaotropic salts are sodium iodide, sodium perchlorate, guanidine thiocyanate, guanidine isothiocyanate or guanidine hydrochloride. Other compounds known to the skilled artisan are also possible. A chaotropic agent of the present invention is any chemical substance which disturbs the ordered structure of liquid water and has the effect that DNA or RNA binds to the magnetic glass particles if this agent is present in the DNA or RNA containing solution. It is obvious for the artisan to produce suitable aqueous buffered solutions. Buffer systems which suitable for molecular biology purposes may be found e.g. in Sambrook, Fritsch & Maniatis, Molecular Cloning, A Laboratory Manual, 3rd edition, CSHL Press, 2001. Typical buffer substances are tris-(hydroxymethyl)-aminomethane (TRIS), phosphate, N-(2-hydroxyethyl)piperazine-N'-(2-ethanesulfonic acid) (HEPES), salts thereof or other suitable substances. Additionally, substances may be present which modify the ionic strength of the solution as, e.g., NaCl, KCl or $CaCl_2$ or which are metal cation complexing agents as, e.g., ethylene-diamine-tetra-acetic acid (EDTA) or the salts thereof. Other biological substances known to the skilled artisan may also be present.

The method of the present invention is suitable for the purification of nucleic acids, i.e. RNA or DNA, from complex mixtures with other biological substances containing them. Thereby also mixtures of different nucleic acids may be purified, even mixtures containing a nucleic acid of interest in low abundance. Thus, the present invention also encompasses the purification of mixtures of specific nucleic acids in which the target nucleic acid(s) may be a minor component in terms of concentration (or may be present in low abundance).

The procedure described can be used to isolate native or modified nucleic acids. Native nucleic acids are understood to be nucleic acids, the structure of which was not irreversibly changed compared with the naturally-occurring nucleic acids. This does not mean that other components of the sample can not be modified, however. Modified nucleic acids include nucleic acids that do not occur in nature, e.g., nucleic acids that are modified by attaching to them groups that are reactive, detectable or capable of immobilization. An example of this is biotinylated nucleic acids.

After the steps described above, the nucleic acids isolated using the methods of the invention can now be used further as necessary. For instance, they can be used as a substrate for various enzymatic reactions. When nucleic acids are involved, they can be used for sequencing, radioactive or non-radioactive labeling, amplification of one or more of the sequences they contain, transcription, hybridization with labeled probe nucleic acids, translation or ligation. Therefore, the invention also encompasses the method comprising the step of releasing the bound target nucleic acids from the material with an affinity thereto. If desired, the target nucleic acid(s) purified in this manner can be separated from the material as described above.

Therefore, a first embodiment of the invention is a method for the purification of a nucleic acid, comprising the steps of a) adsorbing on a substrate the nucleic acid from a composition containing (i) an aqueous buffer, (ii) salts in a high concentration, (iii) a water-miscible, non-acidic organic compound comprising a functional group of the formula

whereby W is a carbon atom or a sulfur atom and Z is an oxygen atom or a nitrogen atom, and (iv) the nucleic acid; b) optionally washing with a washing solution the substrate with the adsorbed nucleic acid; followed by c) contacting the substrate with the adsorbed nucleic acid with a solution containing salts in a lower concentration compared to the composition of step (a), thereby desorbing the nucleic acid from the substrate; and d) separating the solution with the desorbed nucleic acid from the substrate, thereby purifying the nucleic acid; and optionally (e) precipitating the desorbed nucleic acid from the solution of step (d) and isolating the precipitated nucleic acid, thereby further purifying the nucleic acid. It is typical that the functional group is selected from the group consisting of an oxo group, a sulfoxo group, a cyano group, and a carbonyl group of a carbamoyl function or an amide but not belonging to a carboxy function. It is even more typical that the water-miscible, non-acidic organic compound is selected from the group consisting of acetone, acetylacetone, acetonitrile, dimethylsulfoxide, diethylketone, methylethylketone, methylpropylketone, isobutylmethylketone, gamma-butyrolactone, gamma-valerolactone, propylene carbonate, and N-methyl-2-pyrrolidone. It is also contemplated that the composition of step (a) is made use of in automated processes for the purification of a (at least one) nucleic acid. Automatic processing devices capable of performing the methods of the invention, such as robots with a pipetting device, often have open vessels that contain solutions, e.g. stock solutions. In this regard it is advantageous that the liquid phases of the solutions contain a solvent which under normal atmospheric pressure and room temperature has a low tendency to evaporate. Therefore, very typically, the water-miscible, non-acidic organic compound is dimethylsulfoxide. Also very typically, the water-miscible, non-acidic organic compound is N-methyl-2-pyrrolidone.

Typically, the composition of step (a) contains 1 to 50 percent volume by volume of the water-miscible, non-acidic organic compound. More typically, the composition of step (a) contains 2 to 35 percent volume by volume of the water-miscible, non-acidic organic compound. Even more typically, the composition of step (a) contains 3 to 30 percent volume by volume of the water-miscible, non-acidic organic compound. Very typically, the composition of step (a) contains about 4 percent volume by volume of the water-miscible, non-acidic organic compound. Very typically, the composition of step (a) contains about 15 percent volume by volume of the water-miscible, non-acidic organic compound. Very typically, the composition of step (a) contains about 25 percent volume by volume of the water-miscible, non-acidic organic compound.

Typically, the salts in the composition of step (a) are chaotropic salts in concentrations of 1 to 8 M. More typically, said chaotropic salts are selected from the group consisting of sodium perchlorate, guanidine hydrochloride, guanidine thiocyanate, guanidine isothiocyanate, and sodium iodide.

Also typically, the salts in the composition of step (a) are in concentrations of 1 to 10 M and said salts are selected from the group consisting of lithium chloride, sodium chloride, potassium chloride, sodium acetate, urea, and mixtures thereof.

Typically, the washing solution contains the water-miscible, non-acidic organic compound. More typically, the washing solution contains 1 to 50 percent volume by volume of the water-miscible, non-acidic organic compound. Even more typically, the washing solution contains 2 to 35 percent volume by volume of the water-miscible, non-acidic organic compound. Even more typically, the washing solution contains 3 to 30 percent volume by volume of the water-miscible, non-acidic organic compound. Very typically, the washing solution contains about 4 percent volume by volume of the water-miscible, non-acidic organic compound. Very typically, the washing solution contains about 15 percent volume by volume of the water-miscible, non-acidic organic compound. Very typically, the washing solution contains about 25 percent volume by volume of the water-miscible, non-acidic organic compound.

Typically, the substrate comprises a porous or non-porous mineral substrate selected from the group consisting of silica gel, glass fibers, quartz fibers, and zeolites. Also typically, the substrate comprises a porous or non-porous mineral substrate selected from the group consisting of metal oxides, and/or metal mixed oxides, alumina, titania, zirconia, and materials predominantly consisting of glass. It is also typical that the mineral substrate has a particle size of 0.1 μm to 1,000 μm. It is also typical that porous mineral support materials, when employed, have a pore size of from 2 to 1,000 nm. More typically, porous or non-porous support materials, especially zeolites, are in the form of loose packings. Even more typically, the mineral substrate consists of filter sheets in the form of glass, quartz or ceramic filter sheets, and/or a membrane containing silica gel and/or particles or fibers of mineral supports and fabrics of quartz or glass wool. It is also typical that the substrate comprises magnetically attractable particles. More typically, the magnetically attractable particles are coated with a mineral substrate selected from the group consisting of silica gel, glass, quartz, and zeolites. Even more typically, the substrate comprises magnetically attractable particles coated with glass. The target nucleic acid(s) can be detected and determined. The above-described purification method is typical, followed by a determination or detection step or purification methods followed by an amplification and determination or detection step. The target nucleic acid or nucleic acids of interest may be contained in a matrix of non-target nucleic acids, and may even be a minor component in said mixture of specific nucleic acids. Suitable DNA detection methods are known to the skilled artisan and are described in standard textbooks as Sambrook, Fritsch & Maniatis, Molecular Cloning, A Laboratory Manual, 3rd edition, CSHL Press, 2001; and Ausubel et al., Current Protocols in Molecular Biology, J. Wiley and Sons, New York, 1987. There may be also further purification steps before the DNA detection step is carried out as e.g. a precipitation step. The detection methods may include but are not limited to the binding or intercalating of specific dyes as ethidium bromide which intercalates into the double-stranded DNA and changes its fluorescence thereafter. The purified DNA may also be separated by electrophoretic methods, optionally after a restriction digest, and visualized thereafter. There are also probe-based assays which exploit the oligonucleotide hybridization to specific sequences and subsequent detection of the hybrid. It is also possible to sequence the DNA after further steps known to the skilled artisan. Other methods apply a diversity of DNA sequences to a silicon chip to which specific probes are bound and yield a signal when a complementary sequences bind.

The invention also encompasses the mixture of non-proteinaceous and proteinaceous components comprising nucleic acids whereby the nucleic acids comprise DNA or RNA or both.

The invention also encompasses biological samples, from which nucleic acids are purified, comprising viruses or bacterial cells, as well as isolated cells from multicellular organisms as e.g. human and animal cells such as leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. The present invention also encompasses biological samples such as a fluid from the human or animal body; typically the biological sample is blood, blood plasma, blood serum or urine. The blood plasma is typically EDTA, heparin or citrate blood plasma. In an embodiment of the invention the biological sample comprises bacterial cells, eukaryotic cells, viruses or mixtures thereof. A biological sample as exemplified above, typically in a processed form such as a lysate, can be part of the composition from which the (target) nucleic acid is adsorbed to the substrate.

It is also typical that the mixture of nucleic acids and proteinaceous material comprises deoxyribonucleic acid (DNA) or ribonucleic acid (RNA) or both, typically the DNA or RNA or both is derived from a virus or a (at least one) microorganism. The virus can be hepatitis A virus (HAV), hepatitis B virus (HBV), hepatitis C virus (HCV), the human immunodeficiency virus (HIV), the human papilloma virus (HPV) or parvovirus B19.

It is also typical that a target nucleic acid component and the other nucleic acids are purified essentially as described above. Then the target nucleic acid component is further manipulated and detected, i.e. it is amplified with the polymerase chain reaction which specifically amplifies target sequences to detectable amounts. Other possible amplification reactions are the ligase Chain Reaction (LCR, Wu, D. Y., and Wallace, R. B., Genomics 4 (1989) 560-569, and Barany, F., Proc. Natl. Acad. Sci. USA 88 (1991) 189-193); Polymerase Ligase Chain Reaction (Barany, F., PCR Methods and Applic. 1 (1991) 5-16); Gap-LCR (PCT Patent Publication No. WO 90/01069); Repair Chain Reaction (European Patent Publication No. EP 0 439 182 A2), 3SR (Kwoh, D. Y., et al., Proc. Natl. Acad. Sci. USA 86 (1989) 1173-1177; Guatelli, J. C., et al., Proc. Natl. Acad. Sci. USA 87 (1990) 1874-1878; PCT Patent Publication No. WO 92/08800), and NASBA (U.S. Pat. No. 5,130,238). Further, there are strand displacement amplification (SDA), transcription mediated amplification (TMA), and Q-beta-amplification (for a review see e.g. Whelen, A. C., and Persing, D. H., Annu. Rev. Microbiol. 50 (1996) 349-373; Abramson, R. D., and Myers, T. W., Curr. Opin. Biotechnol. 4 (1993) 41-47).

Particularly typical is the TAQMAN detection method disclosed in WO 92/02638 and the corresponding US patents U.S. Pat. No. 5,210,015; U.S. Pat. No. 5,804,375; U.S. Pat. No. 5,487,972. This method exploits the exonuclease activity of a polymerase to generate a signal. In detail, the target nucleic acid component is detected by a process comprising contacting the sample with an oligonucleotide containing a sequence complementary to a region of the target nucleic acid component and a labeled oligonucleotide containing a sequence complementary to a second region of the same target nucleic acid component sequence strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. TAQMAN technology eliminates the need for a solid phase bound reaction complex to be formed and made detectable. In more general terms, a procedure for the purification of a target nucleic acid component followed by a detection step is disclosed wherein the amplification and/or detection reaction is a homogeneous solution-phase.

Another embodiment of the invention is a method for adsorbing a nucleic acid on a substrate, comprising the steps of (a) providing the nucleic acid in an aqueous solution containing salts in a high concentration and a water-miscible, non-acidic organic compound comprising a functional group of the formula W═Z whereby W is a carbon atom or a sulfur atom and Z is an oxygen atom or a nitrogen atom; and (b) adding the aqueous solution of step (a) to the substrate. Typically, the functional group is selected from the group consisting of an oxo group, a sulfoxo group, a cyano group, and a carbonyl group of a carbamoyl function or an amide but not belonging to a carboxy function. More typically, the water-miscible, non-acidic organic compound is selected from the group consisting of acetone, acetylacetone, acetonitrile, dimethylsulfoxide, diethylketone, methylethylketone, methylpropylketone, isobutylmethylketone, gamma-butyrolactone, gamma-valerolactone, propylene carbonate, and N-methyl-2-pyrrolidone. It is also contemplated that the aqueous solution of step (a) is made use or in automated processes for the purification of a (at least one) nucleic acid. Automatic processing devices capable of performing a method of the invention, such as robots with a pipetting device, often have open vessels that contain solutions, e.g. stock solutions. In this regard it is advantageous that the liquid phases of the solutions and/or suspensions contain a solvent which under normal atmospheric pressure and room temperature has a low tendency to evaporate. Therefore, very typically, the water-miscible, non-acidic organic compound is dimethylsulfoxide. Also very typically, the water-miscible, non-acidic organic compound is N-methyl-2-pyrrolidone.

Typically, the aqueous solution of step (a) contains 1 to 50 percent volume by volume of the water-miscible, non-acidic organic compound. More typically, the aqueous solution of step (a) contains 2 to 35 percent volume by volume of the water-miscible, non-acidic organic compound. Even more typically, the aqueous solution of step (a) contains 3 to 30 percent volume by volume of the water-miscible, non-acidic organic compound. Very typically, the aqueous solution of step (a) contains about 4 percent volume by volume of the water-miscible, non-acidic organic compound. Very typically, the aqueous solution of step (a) contains about 15 percent volume by volume of the water-miscible, non-acidic organic compound. Very typically, the aqueous solution of step (a) contains about 25 percent volume by volume of the water-miscible, non-acidic organic compound.

Typically, the salts in the aqueous solution of step (a) are chaotropic salts in concentrations of 1 to 8 M. More typically, said chaotropic salts are selected from the group consisting of sodium perchlorate, guanidine hydrochloride, guanidine thiocyanate, guanidine isothiocyanate, and sodium iodide.

Also typically, the salts in the aqueous solution of step (a) are in concentrations of 1 to 10 M and said salts are selected from the group consisting of lithium chloride, sodium chloride, potassium chloride, sodium acetate, urea, and mixtures thereof.

Typically, the substrate comprises a porous or non-porous mineral substrate selected from the group consisting of silica gel, glass fibers, quartz fibers, and zeolites. Also typically, the substrate comprises a porous or non-porous mineral substrate selected from the group consisting of metal oxides, and/ or metal mixed oxides, alumina, titania, zirconia, and materials predominantly consisting of glass. It is also typical that the mineral substrate has a particle size of 0.1 µm to 1,000 µm. It is also typical that porous mineral support materials, when employed, have a pore size of from 2 to 1,000 nm. More typically, porous or non-porous support materials, especially zeolites, are in the form of loose packings. Even more typically, the mineral substrate consists of filter sheets in the form of glass, quartz or ceramic filter sheets, and/ or a membrane containing silica gel and/ or particles or fibers of mineral supports and fabrics of quartz or glass wool. It is also typical that the substrate comprises magnetically attractable particles. More typically, the magnetically attractable particles are coated with a mineral substrate selected from the group consisting of silica gel, glass, quartz, and zeolites. Even more typically, the substrate comprises magnetically attractable particles coated with glass.

Yet another embodiment of the invention is a method for adsorbing a nucleic acid on a substrate, comprising the steps of (a) providing the nucleic acid in an aqueous solution containing salts in a high concentration; (b) providing the substrate in the form of powdered material; (c) providing a water-miscible, non-acidic organic compound comprising a functional group of the formula W═Z whereby W is a carbon atom or a sulfur atom and Z is an oxygen atom or a nitrogen atom; (d) dispersing the substrate of step (b) in the water-miscible, non-acidic organic compound of step (c) to form a suspension of said substrate; and (e) mixing the aqueous solution of step (a) with the suspension of step (d). Typically, the functional group is selected from the group consisting of an oxo group, a sulfoxo group, a cyano group, and a carbonyl group of a carbamoyl function or an amide but not belonging to a carboxy function. More typically, the water-miscible, non-acidic organic compound is selected from the group consisting of acetone, acetylacetone, acetonitrile, dimethylsulfoxide, diethylketone, methylethylketone, methylpropylketone, isobutylmethylketone, gamma-butyrolactone, gamma-valerolactone, propylene carbonate, and N-methyl-2-pyrrolidone. It is also contemplated that the suspension of step (d) is used in automated processes for the purification of a (at least one) nucleic acid. Automatic processing devices capable of performing a method of the invention, such as robots with a pipetting device, often have open vessels that contain solutions, e.g., stock solutions, and suspensions such as the suspension of step (d). In this regard it is advantageous that the liquid phases of the solutions and/ or suspensions contain a solvent which under normal atmospheric pressure and room temperature has a low tendency to evaporate. Therefore, very typically, the water-miscible, non-acidic organic compound is dimethylsulfoxide. Also very typically, the water-miscible, non-acidic organic compound is N-methyl-2-pyrrolidone.

Typically, the composition of step (e) contains 1 to 50 percent volume by volume of the water-miscible, non-acidic organic compound. More typically, the composition of step (e) contains 2 to 35 percent volume by volume of the water-miscible, non-acidic organic compound. Even more typically, the composition of step (e) contains 3 to 30 percent volume by volume of the water-miscible, non-acidic organic compound. Even more typically, the composition of step (e) contains about 4 percent volume by volume of the water-miscible, non-acidic organic compound. Even more typically, the composition of step (e) contains about 15 percent volume by volume of the water-miscible, non-acidic organic compound. Even more typically, the composition of step (e) contains about 25 percent volume by volume of the water-miscible, non-acidic organic compound.

Typically, the salts in the composition of step (e) are chaotropic salts in concentrations of 1 to 8 M. More typically, said chaotropic salts are selected from the group consisting of sodium perchlorate, guanidine hydrochloride, guanidine thiocyanate, guanidine isothiocyanate, and sodium iodide.

Also typically, the salts in the composition of step (e) are in concentrations of 1 to 10 M and said salts are selected from the group consisting of lithium chloride, sodium chloride, potassium chloride, sodium acetate, urea, and mixtures thereof.

Typically, the substrate comprises a powdered porous or non-porous mineral substrate selected from the group consisting of silica gel, glass, quartz, and zeolites. Also typically, the substrate comprises a powdered porous or non-porous mineral substrate selected from the group consisting of metal oxides, and/ or metal mixed oxides, alumina, titania, zirconia, and materials predominantly consisting of glass. It is also typical that the substrate comprises magnetically attractable particles. More typically, the magnetically attractable particles are coated with a mineral substrate selected from the group consisting of silica gel, glass, quartz, and zeolites. Even more typically, the substrate comprises magnetically attractable particles coated with glass.

Yet another embodiment of the invention is a suspension containing a substrate in the form of powdered material dispersed in a water-miscible, non-acidic organic compound comprising a functional group of the formula W≡≡≡Z whereby W is a carbon atom or a sulfur atom and Z is an oxygen atom or a nitrogen atom. Typically, the functional group is selected from the group consisting of an oxo group, a sulfoxo group, a cyano group, and a carbonyl group of a carbamoyl function or an amide but not belonging to a carboxy function. More typically, the water-miscible, non-acidic organic compound is selected from the group consisting of acetone, acetylacetone, acetonitrile, dimethylsulfoxide, diethylketone, methylethylketone, methylpropylketone, isobutylmethylketone, gamma-butyrolactone, gamma-valerolactone, propylene carbonate, and N-methyl-2-pyrrolidone. It is also contemplated that the suspension of the invention is used in automated processes for the purification of a (at least one) nucleic acid. Automatic processing devices capable of performing a method of the invention, such as robots with a pipetting device, often have open vessels that contain solutions, e.g. stock solutions, and suspensions such as the suspension mentioned above. In this regard it is advantageous that the liquid phases of the solutions and/or suspensions contain a solvent which under normal atmospheric pressure and room temperature has a low tendency to evaporate. Therefore, very typically, the water-miscible, non-acidic organic compound is dimethylsulfoxide. Also very typically, the water-miscible, non-acidic organic compound is N-methyl-2-pyrrolidone.

Typically, the substrate comprises a powdered porous or non-porous mineral substrate selected from the group consisting of silica gel, glass, quartz, and zeolites. Also typically, the substrate comprises a powdered porous or non-porous mineral substrate selected from the group consisting of metal oxides, and/or metal mixed oxides, alumina, titania, zirconia, and materials predominantly consisting of glass. It is also typical that the substrate comprises magnetically attractable particles. More typically, the magnetically attractable particles are coated with a mineral substrate selected from the group consisting of silica gel, glass, quartz, and zeolites. Even more typically, the substrate comprises magnetically attractable particles coated with glass.

Yet another embodiment of the invention is the use of a water-miscible, non-acidic organic compound comprising a functional group of the formula W≡≡≡Z whereby W is a carbon atom or a sulfur atom and Z is an oxygen atom or a nitrogen atom, for performing the methods of the invention described herein.

Typically, the functional group is selected from the group consisting of an oxo group, a sulfoxo group, a cyano group, and a carbonyl group of a carbamoyl function or an amide but not belonging to a carboxy function. More typically, the water-miscible, non-acidic organic compound is selected from the group consisting of acetone, acetylacetone, acetonitrile, dimethylsulfoxide, diethylketone, methylethylketone, methylpropylketone, isobutylmethylketone, gamma-butyrolactone, garuna-valerolactone, propylene carbonate, and N-methyl-2-pyrrolidone. It is also contemplated that the suspension of the invention is used in automated processes for the purification of a (at least one) nucleic acid. Automatic processing devices capable of performing a method of the invention, such as robots with a pipetting device, often have open vessels that contain solutions, e.g. stock solutions, and suspensions such as the suspension mentioned above. In this regard it is advantageous that the liquid phases of the solutions and/or suspensions contain a solvent which under normal atmospheric pressure and room temperature has a low tendency to evaporate. Therefore, very typically, the water-miscible, non-acidic organic compound is dimethylsulfoxide. Also very typically, the water-miscible, non-acidic organic compound is N-methyl-2-pyrrolidone.

Yet another embodiment of the invention is the use of a water-miscible, non-acidic organic compound comprising a functional group of the formula W≡≡≡Z whereby W is a carbon atom or a sulfur atom and Z is an oxygen atom or a nitrogen atom, for preparing a suspension by way of dispersing a substrate in said water-miscible, non-acidic organic compound to form a suspension of said substrate.

Typically, the functional group is selected from the group consisting of an oxo group, a sulfoxo group, a cyano group, and a carbonyl group of a carbamoyl function or an amide but not belonging to a carboxy function. More typically, the water-miscible, non-acidic organic compound is selected from the group consisting of acetone, acetylacetone, acetonitrile, dimethylsulfoxide, diethylketone, methylethylketone, methylpropylketone, isobutylmethylketone, gamma-butyrolactone, gamma-valerolactone, propylene carbonate, and N-methyl-2-pyrrolidone. It is also contemplated that the suspension of the invention is used in automated processes for the purification of a (at least one) nucleic acid. Automatic processing devices capable of performing a method of the invention, such as robots with a pipetting device, often have open vessels that contain solutions, e.g. stock solutions, and suspensions such as the suspension mentioned above. In this regard it is advantageous that the liquid phases of the solutions and/or suspensions contain a solvent which under normal atmospheric pressure and room temperature has a low tendency to evaporate. Therefore, very typically, the water-miscible, non-acidic organic compound is dimethylsulfoxide. Also very typically, the water-miscible, non-acidic organic compound is N-methyl-2-pyrrolidone.

Typically, the substrate comprises a powdered porous or non-porous mineral substrate selected from the group consisting of silica gel, glass, quartz, and zeolites. Also typically, the substrate comprises a powdered porous or non-porous mineral substrate selected from the group consisting of metal oxides, and/or metal mixed oxides, alumina, titania, zirconia, and materials predominantly consisting of glass. It is also typical that the substrate comprises magnetically attractable particles. More typically, the magnetically attractable particles are coated with a mineral substrate selected from the group consisting of silica gel, glass, quartz, and zeolites. Even more typically, the substrate comprises magnetically attractable particles coated with glass.

Yet another embodiment of the invention is the use of a suspension of the invention for performing a method of the invention as described herein.

The invention also contemplates kits. Such kits known in the art further comprise plastics ware which can be used during the sample preparation procedure as e.g. microtiter plates in the 96 or 384 well format or just ordinary reaction tubes manufactured e.g. by Eppendorf, Hamburg, Germany, and all other reagents for carrying out the methods of the invention. Therefore, the kit can additionally contain a material with an affinity to nucleic acids (and the (at least one) target nucleic acid component), typically the material with an affinity to nucleic acids (and the (at least one) target nucleic acid component) comprises a material with a silica surface. Typically, the material with a silica surface is a glass. Most typically, the material with an affinity to nucleic acids is a composition comprising magnetic glass particles, i.e., magnetically attractable particles coated with glass. Another typical material with an affinity to nucleic acids is an anion exchanger. The kit can further or additionally comprise a lysis buffer containing, e.g., chaotropic agents, detergents, or mixtures thereof which allows the lysis of cells. These components of the kit of the invention may be provided separately in tubes or storage containers. Depending on the nature of the components, these may be even provided in a single tube or storage container. The kit may further or additionally comprise a washing solution which is suitable for the washing step of the magnetic glass particles when DNA or RNA is bound thereto. This washing solution may contain a water-miscible, non-acidic organic compound of the invention and/or chaotropic agents in a buffered solution or solutions with an acidic pH without a water-miscible, non-acidic organic compound of the invention and/or chaotropic agents as described above. Often the washing solution or other solutions are provided as stock solutions which have to be diluted before use. The kit may further or additionally comprise an eluent or elution buffer, i.e. a solution or a buffer (e.g. 10 mM tris, 1 mM EDTA, pH 8.0) or pure water to elute the DNA or RNA bound to the magnetic glass particles. Further, additional reagents or buffered solutions may be present which can be used for the purification process of a nucleic acid, i.e. DNA or RNA.

Yet another embodiment of the invention is a kit of parts, containing (a) a concentrated stock solution of a buffer salt and a chaotiropic salt selected from the group consisting of sodium perchlorate, guanidine hydrochloride, guanidine thiocyanate, guanidine isothiocyanate, and sodium iodide; (b) a water-miscible, non-acidic organic compound comprising a functional group of the formula w===Z whereby W is a carbon atom or a sulfur atom and Z is an oxygen atom or a nitrogen atom and the water-miscible, non-acidic organic compound is selected from the group consisting of acetone, acetylacetone, acetonitrile, dimethylsulfoxide, diethylketone, methylethylketone, methylpropylketone, isobutylmethylketone, gamma-butyrolactone, gamma-valerolactone, propylene carbonate, and N-methyl-2-pyrrolidone; (c) buffer solutions; and (d) chromatographic and filtering material.

Yet another embodiment of the invention is a kit of parts, containing (a) a concentrated stock solution of a buffer salt and a salt selected from the group consisting of lithium chloride, sodium chloride, potassium chloride, sodium acetate, urea, and mixtures thereof; (b) a water-miscible, non-acidic organic compound comprising a functional group of the formula W===Z whereby W is a carbon atom or a sulfur atom and Z is an oxygen atom or a nitrogen atom and the water-miscible, non-acidic organic compound is selected from the group consisting of acetone, acetylacetone, acetonitrile, dimethylsulfoxide, diethylketone, methylethylketone, methylpropylketone, isobutylmethylketone, gamma-butyrolactone, gamma-valerolactone, propylene carbonate, and N-methyl-2-pyrrolidone; (c) buffer solutions; and (d) chromatographic and filtering material.

Yet another embodiment of the invention is a kit of parts, containing (a) a concentrated stock solution of a buffer salt and a chaotropic salt selected from the group consisting of sodium perchlorate, guanidine hydrochloride, guanidine thiocyanate, guanidine isothiocyanate, and sodium iodide; (b) a suspension of the invention described above; (c) buffer solutions.

Yet another embodiment of the invention is a kit of parts, containing (a) a concentrated stock solution of a buffer salt and a salt selected from the group consisting of lithium chloride, sodium chloride, potassium chloride, sodium acetate, urea, and mixtures thereof; (b) a suspension of the invention described above; (c) buffer solutions.

A typical embodiment of the present invention is to use the methods or the kits of the present invention in automatable methods as e.g. described in WO 99/16781. Automatable method means that the steps of the method are suitable to be carried out with an apparatus or machine capable of operating with little or no external control or influence by a human being. Automatized method means that the steps of the automatable method are carried out with an apparatus or machine capable of operating with little or no external control or influence by a human being. Only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. Typical automatized methods are those which are carried out in a high-throughput format which means that the methods and the used machine or apparatus are optimized for a high-throughput of samples in a short time. In another embodiment of the invention the methods or the kits of the present invention are used in semi-automatized process which means that some reaction steps may have to be done manually. In a typical embodiment of the invention, a suspension containing magnetic glass particles of the present invention is taken from a storage container and partial volumes are added to different reaction vessels. Reaction vessels may be reaction tubes made from plastics eventually in microtiter plate format contain 96 or 384 or more wells where a reaction can be carried out. However, these vessels may be made from other material, e.g. from steel.

It is clear to the skilled artisan that some of the organic compounds contemplated by the invention are capable of dissolving certain plastic materials. Thus, when determining the nature of suitable storage or reaction vessels, the skilled artisan will determine in a limited number of obvious experiments the material which is suited best for executing the methods of the invention or for producing kits of the invention.

In typical embodiments of the invention the kits of the invention are used for the purification of nucleic acids in research, bioanalytics or diagnostics. In typical embodiments of the invention the kits of the invention or the methods of the invention are used in a high-throughput format, i.e. in an automated method which allows the analysis of a high number of different samples in a very short time.

Another embodiment of the invention is a method for determining the presence of a nucleic acid in a biological sample, comprising the steps of (a) lysing the biological sample; (b) forming a composition containing (i) the lysed biological sample of step (a), (ii) an aqueous buffer, (iii) salts in a high concentration, (iv) a water-miscible, non-acidic organic compound comprising a functional group of the formula W===Z whereby W is a carbon atom or a sulfur atom and Z is an oxygen atom or a nitrogen atom; (c) contacting the composition of step (b) with a substrate, thereby adsorbing the nucleic acid to the substrate; (d) optionally washing with a washing solution the substrate with the adsorbed nucleic acid; followed by (e) contacting the substrate with the adsorbed nucleic acid with a solution containing salts in a lower concentration compared to the composition of step (a), thereby desorbing the nucleic acid from the substrate; and (f) separating the solution with the desorbed nucleic acid from the substrate; and (g) detecting in the solution of step (f) the presence of the nucleic acid, thereby determining the presence of the nucleic acid. Typically, the nucleic acid is determined by amplification of the nucleic acid by means of the polymerase chain reaction using specific primers, a specific detection probe, and an amplification mixture, whereby amplification is monitored in real time. Also typical is to determine the nucleic acid by hybridizing the nucleic acid to a hybridization probe and detecting and/or quantifying the hybrid. The skilled artisan is aware of the fact that not only a nucleic acid can serve as a hybridization probe but also a nucleic acid comprising one or more nucleoside analogues can be used. In addition, nucleic acid analogues such as PNA are known to the art as being capable of forming detectable hybrids with nucleic acids. It is understood that the nucleic acid to be determined is DNA or RNA. Very typical is the above method, whereby the nucleic acid is RNA and step (g) comprises (i) reverse transcribing the RNA to form a cDNA, (ii) subsequently amplifying, by means of the polymerase chain reaction, the cDNA, (iii) detecting the presence of the cDNA, thereby determining the presence of the nucleic acid.

It has also been found by the inventors that a water-miscible cyclic diether is a suitable non-acidic organic compound to perform the methods of the invention.

Therefore, another embodiment of the invention is a method for the purification of a nucleic acid, comprising the steps of a) adsorbing on a substrate the nucleic acid from a composition containing (i) an aqueous buffer, (ii) salts in a high concentration, (iii) a water-miscible cyclic diether, and (iv) the nucleic acid; b) optionally washing with a washing solution the substrate with the adsorbed nucleic acid; followed by c) contacting the substrate with the adsorbed nucleic acid with a solution containing salts in a lower concentration compared to the composition of step (a), thereby desorbing the nucleic acid from the substrate; and d) separating the solution with the desorbed nucleic acid from the substrate, thereby purifying the nucleic acid; and optionally (e) precipitating the desorbed nucleic acid from the solution of step (d) and isolating the precipitated nucleic acid, thereby further purifying the nucleic acid. Typically, the water-miscible cyclic diether is dioxane.

Typically, the composition of step (a) contains 1 to 50 percent volume by volume of the water-miscible cyclic diether. More typically, the composition of step (a) contains 2 to 35 percent volume by volume of the water-miscible cyclic diether. Even more typically, the composition of step (a) contains 3 to 30 percent volume by volume of the water-miscible cyclic diether. Very typically, the composition of step (a) contains about 4 percent volume by volume of the water-miscible cyclic diether. Very typically, the composition of step (a) contains about 15 percent volume by volume of the water-miscible cyclic diether. Very typically, the composition of step (a) contains about 25 percent volume by volume of the water-miscible cyclic diether.

Typically, the salts in the composition of step (a) are chaotropic salts in concentrations of 1 to 8 M. More typically, said chaotropic salts are selected from the group consisting of sodium perchlorate, guanidine hydrochloride, guanidine thiocyanate, guanidine isothiocyanate, and sodium iodide.

Also typically, the salts in the composition of step (a) are in concentrations of 1 to 10 M and said salts are selected from the group consisting of lithium chloride, sodium chloride, potassium chloride, sodium acetate, urea, and mixtures thereof.

Typically, the washing solution contains the water-miscible cyclic diether. More typically, the washing solution contains 1 to 50 percent volume by volume of the water-miscible cyclic diether. Even more typically, the washing solution contains 2 to 35 percent volume by volume of the water-miscible cyclic diether. Even more typically, the washing solution contains 3 to 30 percent volume by volume of the water-miscible cyclic diether. Very typically, the washing solution contains about 4 percent volume by volume of the water-miscible cyclic diether. Very typically, the washing solution contains about 15 percent volume by volume of the water-miscible cyclic diether. Very typically, the washing solution contains about 25 percent volume by volume of the water-miscible cyclic diether.

Typically, the substrate comprises a porous or non-porous mineral substrate selected from the group consisting of silica gel, glass fibers, quartz fibers, and zeolites. Also typically, the substrate comprises a porous or non-porous mineral substrate selected from the group consisting of metal oxides, and/or metal mixed oxides, alumina, titania, zirconia, and materials predominantly consisting of glass. It is also typical that the mineral substrate has a particle size of 0.1 µm to 1,000 µm. It is also typical that porous mineral support materials, when employed, have a pore size of from 2 to 1,000 nm. More typically, porous or non-porous support materials, especially zeolites, are in the form of loose packings. Even more typically, the mineral substrate consists of filter sheets in the form of glass, quartz or ceramic filter sheets, and/or a membrane containing silica gel and/or particles or fibers of mineral supports and fabrics of quartz or glass wool. It is also typical that the substrate comprises magnetically attractable particles. More typically, the magnetically attractable particles are coated with a mineral substrate selected from the group consisting of silica gel, glass, quartz, and zeolites. Even more typically, the substrate comprises magnetically attractable particles coated with glass.

Another embodiment of the invention is a method for adsorbing a nucleic acid on a substrate, comprising the steps of (a) providing the nucleic acid in an aqueous solution containing salts in a high concentration and a water-miscible cyclic diether; and (b) adding the aqueous solution of step (a) to the substrate. Typically, the water-miscible cyclic diether is dioxane.

Typically, the aqueous solution of step (a) contains 1 to 50 percent volume by volume of the water-miscible cyclic diether. More typically, the aqueous solution of step (a) contains 2 to 35 percent volume by volume of the water-miscible cyclic diether. Even more typically, the aqueous solution of step (a) contains 3 to 30 percent volume by volume of the water-miscible cyclic diether. Very typically, the aqueous solution of step (a) contains about 4 percent volume by volume of the water-miscible cyclic diether. Very typically, the aqueous solution of step (a) contains about 15 percent volume by volume of the water-miscible cyclic diether. Very typically, the aqueous solution of step (a) contains about 25 percent volume by volume of the water-miscible cyclic diether.

Typically, the salts in the aqueous solution of step (a) are chaotropic salts in concentrations of 1 to 8 M. More typically, said chaotropic salts are selected from the group consisting of sodium perchlorate, guanidine hydrochloride, guanidine thiocyanate, guanidine isothiocyanate, and sodium iodide.

Also typically, the salts in the aqueous solution of step (a) are in concentrations of 1 to 10 M and said salts are selected from the group consisting of lithium chloride, sodium chloride, potassium chloride, sodium acetate, urea, and mixtures thereof.

Typically, the substrate comprises a porous or non-porous mineral substrate selected from the group consisting of silica gel, glass fibers, quartz fibers, and zeolites. Also typically, the substrate comprises a porous or non-porous mineral substrate selected from the group consisting of metal oxides, and/or metal mixed oxides, alumina, titania, zirconia, and materials predominantly consisting of glass. It is also typical that the mineral substrate has a particle size of 0.1 µm to 1,000 µm. It is also typical that porous mineral support materials, when employed, have a pore size of from 2 to 1,000 nm. More typically, porous or non-porous support materials, especially zeolites, are in the form of loose packings. Even more typically, the mineral substrate consists of filter sheets in the form of glass, quartz or ceramic filter sheets, and/or a membrane containing silica gel and/or particles or fibers of mineral supports and fabrics of quartz or glass wool. It is also typical that the substrate comprises magnetically attractable particles. More typically, the magnetically attractable particles are coated with a mineral substrate selected from the group consisting of silica gel, glass, quartz, and zeolites. Even more typically, the substrate comprises magnetically attractable particles coated with glass.

Yet another embodiment of the invention is a method for adsorbing a nucleic acid on a substrate, comprising the steps of (a) providing the nucleic acid in an aqueous solution containing salts in a high concentration; (b) providing the substrate in the form of powdered material; (c) providing a water-miscible cyclic diether; (d) dispersing the substrate of step (b) in the water-miscible cyclic diether of step (c) to form a suspension of said substrate; and (e) mixing the aqueous solution of step (a) with the suspension of step (d). Typically, the water-miscible cyclic diether is dioxane.

Typically, the composition of step (e) contains 1 to 50 percent volume by volume of the water-miscible cyclic diether. More typically, the composition of step (e) contains 2 to 35 percent volume by volume of the water-miscible cyclic diether. Even more typically, the composition of step (e) contains 3 to 30 percent volume by volume of the water-miscible cyclic diether. Even more typically, the composition of step (e) contains about 4 percent volume by volume of the water-miscible cyclic diether. Even more typically, the composition of step (e) contains about 15 percent volume by volume of the water-miscible cyclic diether. Even more typically, the composition of step (e) contains about 25 percent volume by volume of the water-miscible cyclic diether.

Typically, the salts in the composition of step (e) are chaotropic salts in concentrations of 1 to 8 M. More typically, said chaotropic salts are selected from the group consisting of sodium perchlorate, guanidine hydrochloride, guanidine thiocyanate, guanidine isothiocyanate, and sodium iodide.

Also typically, the salts in the composition of step (e) are in concentrations of 1 to 10 M and said salts are selected from the group consisting of lithium chloride, sodium chloride, potassium chloride, sodium acetate, urea, and mixtures thereof.

Typically, the substrate comprises a powdered porous or non-porous mineral substrate selected from the group consisting of silica gel, glass, quartz, and zeolites. Also typically, the substrate comprises a powdered porous or non-porous mineral substrate selected from the group consisting of metal oxides, and/or metal mixed oxides, alumina, titania, zirconia, and materials predominantly consisting of glass. It is also typical that the substrate comprises magnetically attractable particles. More typically, the magnetically attractable particles are coated with a mineral substrate selected from the group consisting of silica gel, glass, quartz, and zeolites. Even more typically, the substrate comprises magnetically attractable particles coated with glass.

Yet another embodiment of the invention is a suspension containing a substrate in the form of powdered material dispersed in a water-miscible cyclic diether. Typically, the water-miscible cyclic diether is dioxane.

Typically, the substrate comprises a powdered porous or non-porous mineral substrate selected from the group consisting of silica gel, glass, quartz, and zeolites. Also typically, the substrate comprises a powdered porous or non-porous mineral substrate selected from the group consisting of metal oxides, and/or metal mixed oxides, alumina, titania, zirconia, and materials predominantly consisting of glass. It is also typical that the substrate comprises magnetically attractable particles. More typically, the magnetically attractable particles are coated with a mineral substrate selected from the group consisting of silica gel, glass, quartz, and zeolites. Even more typically, the substrate comprises magnetically attractable particles coated with glass.

Yet another embodiment of the invention is the use of a water-miscible cyclic diether, for performing the methods of the invention described herein. Typically, the cyclic diether is dioxane.

Yet another embodiment of the invention is the use of a water-miscible cyclic diether, for preparing a suspension by way of dispersing a substrate in said water-miscible cyclic diether to form a suspension of said substrate. Typically, the cyclic diether is dioxane.

Typically, the substrate comprises a powdered porous or non-porous mineral substrate selected from the group consisting of silica gel, glass, quartz, and zeolites. Also typically, the substrate comprises a powdered porous or non-porous mineral substrate selected from the group consisting of metal oxides, and/or metal mixed oxides, alumina, titania, zirconia, and materials predominantly consisting of glass. It is also typical that the substrate comprises magnetically attractable particles. More typically, the magnetically attractable particles are coated with a mineral substrate selected from the group consisting of silica gel, glass, quartz, and zeolites. Even more typically, the substrate comprises magnetically attractable particles coated with glass.

Yet another embodiment of the invention is the use of a suspension in dioxane of the invention and described above for performing a method of the invention as described herein.

Yet another embodiment of the invention is a kit of parts, containing (a) a concentrated stock solution of a buffer salt and a chaotropic salt selected from the group consisting of sodium perchlorate, guanidine hydrochloride, guanidine thiocyanate, guanidine isothiocyanate, and sodium iodide; (b) dioxane; (c) buffer solutions; and (d) chromatographic and filtering material.

Yet another embodiment of the invention is a kit of parts, containing (a) a concentrated stock solution of a buffer salt and a salt selected from the group consisting of lithium chloride, sodium chloride, potassium chloride, sodium acetate, urea, and mixtures thereof; (b) dioxane; (c) buffer solutions; and (d) chromatographic and filtering material.

Yet another embodiment of the invention is a kit of parts, containing (a) a concentrated stock solution of a buffer salt and a chaotropic salt selected from the group consisting of sodium perchlorate, guanidine hydrochloride, guanidine thiocyanate, guanidine isothiocyanate, and sodium iodide; (b) a suspension in dioxane of the invention described above; (c) buffer solutions.

Yet another embodiment of the invention is a kit of parts, containing (a) a concentrated stock solution of a buffer salt and a salt selected from the group consisting of lithium chloride, sodium chloride, potassium chloride, sodium acetate, urea, and mixtures thereof; (b) a suspension in dioxane of the invention described above; (c) buffer solutions.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

In order that the invention may be more readily understood, reference is made to the following examples, which are intended to illustrate the invention but not limit the scope thereof.

Specific Embodiments

EXAMPLE 1

DNA Isolation Using Glass Fiber 1,000 µl of whole blood from a healthy donor was incubated with 100 µl proteinase K solution (Roche product no. 745723; 90 mg dissolved in 4.5 ml water) and 1,200 µl chaotropic binding buffer (6 M guanidinium-HCl, 10 mM trisHCl, 20% Triton X100 pH 4.4) at 70° C. for 10 minutes.

After adding 500 µl of (a) isopropanol, (b) acetonitrile, (c) dimethylsulfoxide or (d) methylethylketone, the lysate was transferred to a glass fiber filter tube (filter tube taken from the kit of Macherey and Nagel Cat. No. 740 954.20). After centrifugation for 3 minutes at 1,900×g the flowthrough was discarded and the filter tube was placed on a collection tube. 2,000 µl of a high ionic inhibitor removal buffer (5M guanidinium-HCl, 20 mM tris, 60% Ethanol, pH 6.6) was pipetted on the glass fiber filter and centrifuged for 1 minute at 3,000×g. Followed by two washing steps with 2,000 µl wash buffers (20 mM NaCl, 2 mM trisHCl, 80% ethanol, pH 7.5) and centrifugation for 5 minutes at 3,000×g. The flowthrough was discarded. A new collection tube was used. The elution of the DNA was done with 300 µl of 70° C. hot tris buffer (10 mM, pH 8.5). After a incubation time of 5 minutes the tube was centrifuged for 5 minutes at 3,000×g.

Analysis of the Isolated DNA

The DNA yields were calculated from the OD260 nm measurement using a standard photometer. The purity was assessed by calculating the ratio OD260/280 nm. The results (n=2) are depicted in Table 1.

TABLE 1

Isolation of DNA from 1,000 µl whole blood

| Adsorption to the substrate in the presence of | Yield (measured by determining OD at 260 nm) | Purity (ratio 260/280 nm) |
|---|---|---|
| isopropanol | 24.1 µg/ml blood | 1.89 |
| acetonitrile | 22.2 µg/ml blood | 1.88 |
| dimethylsufoxide | 23.5 µg/ml blood | 1.90 |
| methylethylketone | 33.5 µg/ml blood | 1.81 |

EXAMPLE 2

RNA Isolation on the MAGNAPURE LC Instrument $10^6$ Hela cells (in a volume of 200 µl) were directly transferred to the sample cartridge of the MAGNAPURE LC instrument (Roche Diagnostics GmbH, Mannheim). The respective protocol was chosen from the software, the necessary plastic disposables and kit reagents were loaded onto the workstation, and the automated RNA isolation was started. The MAGNAPURE LC instrument then automatically performed all isolation and purification steps like cell lysis with a special lysis/binding buffer, enzymatic protein digest with proteinase K, enzymatic DNA digest with DNase I, binding of RNA to magnetic glass particles, several washing steps to remove unbound substances and impurities, elution of the pure RNA in a special elution buffer and finally the transfer of the eluate to a cooled storage cartridge.

When non-acidic organic compounds such as N-methyl-2-pyrrolidone were to be analyzed with respect to their performance in the nucleic acid isolation procedure, dry magnetic glass particles were suspended in a suitable volume of the respective non-acidic organic compound and the suspension was used in the MAGNAPURE LC instrument together with all other reagents of the MAGNAPURE kit (Roche Diagnostics GmbH, Mannheim).

Compared to water, the RNA yield was found to be higher when the suspension of the magnetic glass particles was prepared using N-methyl-2-pyrrolidone. Compared to isopropyl alcohol, the RNA yield was found to be equal or higher when the suspension of the magnetic glass particles was prepared using N-methyl-2-pyrrolidone.

TABLE 2

Figure 1B:
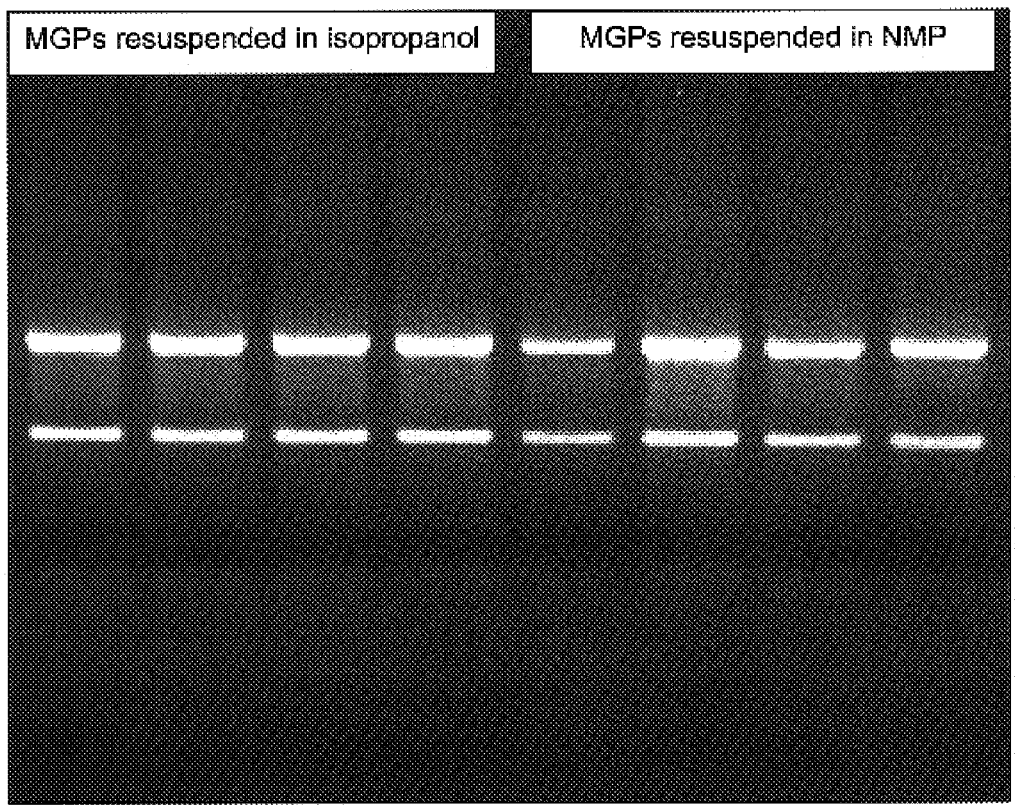
FIG. 1b: RNA was isolated from $10^6$ HeLa cells in 4-fold replicates using the respective protocol and kit of the MAG-NAPURE System (Roche Diagnostics GmbH, Mannheim; catalog no. 3186229). For these isolations, the magnetic glass particles were resuspended either in isopropyl alcohol (isopropanol) or in N-methyl-2-pyrrolidone (NMP). The eluates with purified RNA were then analyzed on an agarose gel.

Isolation of RNA from $10^6$ HeLa cells (see also FIG. 1a, FIG. 1b)

| Magnetic glass particles suspension in | Yield (measured by determining OD at 260 nm) | Purity (ratio 260/280 nm) |
| --- | --- | --- |
| (i) distilled water | 1.97 µg/106 cells | 1.90 |
| (ii) N-methyl-2-pyrrolidone | 15.90 µg/106 cells | 2.02 |
| (iii) N-methyl-2-pyrrolidone | 14.53 µg/106 cells | 2.00 |
| (iv) isopropyl alcohol | 14.31 µg/106 cells | 2.00 |

Results are also shown on FIGS. 1a (i, ii) and 1b (iii, iv).

EXAMPLE 3

DNA Isolation on the MAGNAPURE LC Instrument

Human blood (1 ml) was directly transferred to the sample cartridge of the MAGNAPURE LC instrument (Roche Diagnostics GmbH, Mannheim). The respective protocol was chosen from the software, the necessary plastic disposables and kit reagents were loaded onto the workstation, and the automated DNA isolation was started. The MAGNAPURE LC instrument then automatically performed all isolation and purification steps like cell lysis with a special lysis/binding buffer, enzymatic protein digest with proteinase K, binding of DNA to magnetic glass particles, several washing steps to remove unbound substances and impurities, elution of the pure DNA in a special elution buffer and finally the transfer of the eluate to a cooled storage cartridge.

When non-acidic organic compounds such as N-methyl-2-pyrrolidone were to be analyzed with respect to their performance in the nucleic acid isolation procedure, dry magnetic glass particles were suspended in a suitable volume of the respective non-acidic organic compound and the suspension was used in the MAGNAPURE LC instrument together with all other reagents of the MAGNAPURE kit (Roche Diagnostics GmbH, Mannheim).

Analysis of the Isolated DNA

The integrity of the isolated DNA was checked on a 1% agarose gel, stained with ethidium bromide, together with molecular weight marker III (Roche Diagnostics GmbH, Mannheim). The DNA yields were calculated from the OD260 nm measurement using a standard photometer. The purity was assessed by calculating the ratio OD260/280 nm. To secure that the DNA isolated using the MAGNAPURE protocols and N-methyl-2-pyrrolidone or other non-acidic organic compounds can be amplified, PCR on a LightCycler instrument was performed for all samples using e.g. the LightCycler Factor V Mutation Detection Kit or the LightCycler Her2neu DNA Quantification Kit (both Roche Diagnostics GmbH, Mannheim). Amplification was successful in all cases.

TABLE 3

Figure 2:
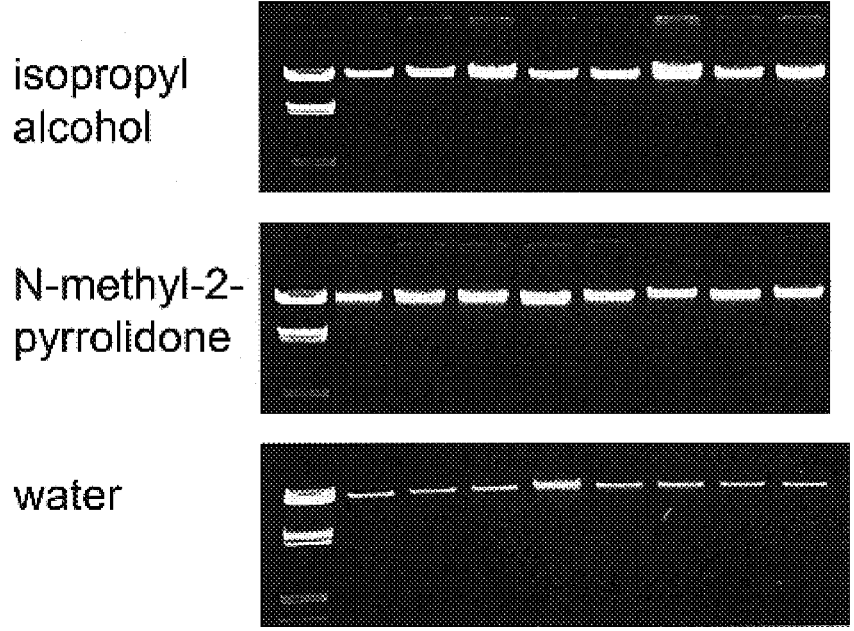
FIG. 2: DNA was isolated from 1 ml of blood in 8-fold replicates using the respective protocol and kit of the MAG-NAPURE System (Roche Diagnostics GmbH, Mannheim; catalog no. 3186229). For these isolations, the magnetic glass particles were resuspended either in Isopropanol or in N-methyl-2-pyrrolidone or in water. The eluates with purified DNA were then analyzed on an agarose gel.

Isolation of DNA from 1,000 µl whole blood (see also FIG. 2)

| Magnetic glass particles suspension in | Yield (measured by determining OD at 260 nm) | Purity (ratio 260/280 nm) |
| --- | --- | --- |
| (i) isopropyl alcohol | 25.3 µg/ml blood | 1.70 |
| (ii) N-methyl-2-pyrrolidone | 26.6 µg/ml blood | 1.75 |
| (iii) water | 7.3 µg/ml blood | 1.69 |

The DNA yield with N-methyl-2-pyrrolidone was the same as with isopropyl alcohol, the yield with water was much lower. FIG. 2 illustrates these results.

EXAMPLE 4

RNA Isolation from a Serum Sample

Lysis and Conditioning

A volume of 200 µl serum from a healthy patient was mixed with 20 µl proteinase K solution (enzyme activity 6,000 U/ml, free of DNase and RNAse activity) and incubated for 5 min at 37° C. Subsequently, 600 µl of lysis buffer was mixed with the proteinase K-treated sample to result in a lysis solution. The lysis buffer contained the following compounds dissolved in water:

TABLE 4

| Quantity | Unit | Substance | Manufacturer | Product no. |
| --- | --- | --- | --- | --- |
| 6.2 | mol/l | guanidinium rhodanide | Fluka | 50981 |
| 0.04 | mol/l | tris HCl pH 7.5 | Fluka | 93372 |
| 10 | g/l | Triton X100 | Fluka | 93426 |
| 0.02 | mol/l | 1,4-Dithio-DL-threit | Fluka | 43816 |
| 15.6 | mg/l | Poly-A | Amersham Biosciences | 27-4110-01 |

Subsequently, 380 µl of a binding conditioner was added to the lysis solution and mixed to result in an adsorption solution. 100% Gamma-butyrolactone (CAS 96-48-0), 100% propylene carbonate (CAS 108-32-7) or 100% 1-methyl-2-pyrrolidone (CAS872-50-4) were used as binding conditioners.

Adsorbing to a Solid Phase

A first 600 µl aliquot of the conditioned lysis solution was transferred to a commercially available spin column with a glass fleece as a solid phase. Typically, High Pure Spin Filter tubes from the High Pure PCR Template Preparation Kit (Roche Diagnostics GmbH, Mannheim, Germany, catalog No. 1796828) were used as spin columns. The spin column with the first 600 µl aliquot was centrifuged at 4,300×g for 1 min. The second aliquot was then transferred to the same spin column and the centrifugation step was repeated under the same conditions.

Washing

The column was washed three times, each time using 150 µl of washing buffer. The washing buffer contained the following compounds dissolved in water:

TABLE 5

| Quantity | Unit | Substance | Manufacturer | Product no. |
|---|---|---|---|---|
| 600 | g/l | Ethanol/isopropanol = 19:1 | Fluka | 2848 |
| 0.66 | mmol/l | trisHCl pH 7.5 | Fluka | 93372 |
| 10 | mg/l | Poly A | Amersham Biosciences | 27-4110-01 |

For the first two washing steps the aliquot of washing buffer was transferred to the spin column and the column was centrifuged at 4,300×g for 1 min. The third washing step was altered in that the column was centrifuged at 13,200×g for 3 min.

Instead of removing the washing buffer by means of centrifugation (third washing step, see above) the solid phase was alternatively dried at 65° C. for 10 min.

Elution

For this step elution buffer was used which contained the following compound dissolved in water:

TABLE 6

| Quantity | Unit | Substance | Manufacturer | Product no. |
|---|---|---|---|---|
| 3.3 | mmol/L | trisHCl pH 7.5 | Fluka | 93372 |

A volume of 150 µl elution buffer was transferred to the spin column and the column was centrifuged at 4,300×g for 1 min. The eluate was collected for further analysis.

EXAMPLE 5

RNA Analysis

Serum samples spiked with 10,000 copies of a positive control target RNA (purified hepatitis C virus RNA) were processed as described in Example 4. The content of target RNA in the eluate was determined by means of TAQMAN PCR using a Roche HCV detection kit.

Figure 3A:
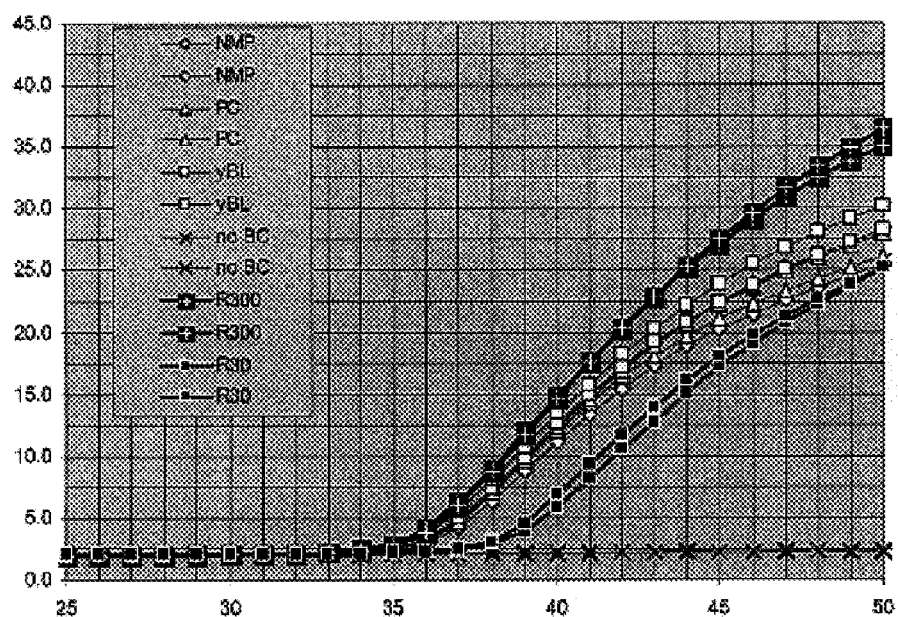
FIGS. 3a, 3b: Fluorescence signal during TAQMAN PCR. The x-axis indicates the number of PCR cycles, the y-axis the fluorescence signal as measured by the detector in [mV]. The "P300" curves reflect the signals obtained with 10,000 copies of positive control target RNA in purified water. The "R30" curves reflect the signals obtained with 1,000 copies of positive control target RNA in purified water. Additional curves are given for "NMP" (1-methyl-2-pyrrolidone), "PC" (propylene carbonate), "yBL" (gamma-butyrolactone), and "no BC" (without the addition of a binding conditioner).
Figure 3B:
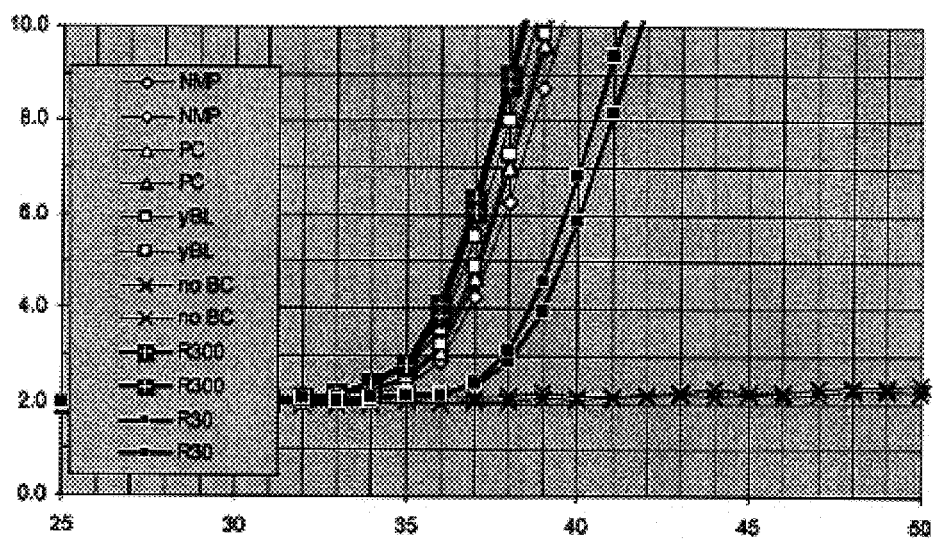

For the calculation of the recovery rate (=amount found after the process/amount before process) standards were run with the detection procedure. FIGS. 3a and 3b show the "R300" curve corresponding to 10,000 copies (i.e. 300% recovery rate) and the "R30" curve corresponding to 1,000 copies (i.e. 30% recovery rate).

FIGS. 3a and 3b illustrate the outcome of a typical experiment. While a control experiment without binding conditioner ("noBC") leads to very low recovery rates (no target found), adding a binding conditioner ("NMP": N-methyl-2-pyrrolidone, "PC": propylene carbonate or "gBL": gamma-butyrolactone) leads to a recovery rate of more than 50% for the control RNA.

Sample preparation procedures which leave impurities in the eluate may impair signal formation during the TAQMAN PCR process. Signal formation was therefore monitored to estimate the quality/purity of the RNA preparation. The value of the fluorescence signal after the last PCR cycle was taken as a measure. As a reference known amounts of clean positive control RNA (the same as spiked to the serum) in pure water was used. FIGS. 3a and 3b illustrate the outcome of a typical experiment. While the formation of fluorescence signal was negligible in the preparations without binding conditioner (mainly due to the missing recovery), adding binding conditioner leads to a improved signal formation which is comparable to the signal formation found with a pure target.

EXAMPLE 6

Sample Processing Time

Samples received from a hospital, whereby the samples had enhanced values of triglycerides, were processed of to following protocol:

A volume of 750 µl Serum was incubated for 5 min with 75 µl proteinase K solution (enzyme activity 6,000 U/ml, free of DNase and RNAse activity) at 37° C. Afterwards, a volume of 1,405 µl lysis buffer (of Table 4) was added and mixed. Subsequently, 880 µl gamma-butyrolactone or, alternatively, 880 µl ethanol 96% were added and mixed, resulting in two different types of adsorption solution.

Each adsorption solution was processed at a constant pressure of +1 bar through a column device containing a glass-fiber-fleece (used from a Roche "High Pure" kit) in a diameter of 5 mm and a thickness of 1 mm. The time for passing of the whole volume through the device (also referred to as "binding time") was measured. The results are summarized in Table 7.

TABLE 7

| Sample-ID | triglyceride content [mmol/Liter] | Binding-time using gamma-butyrolactone [sec] | Binding-time using ethanol [sec] |
|---|---|---|---|
| 3C | 1.78* | 97 | 91 |
| 1C | 3.73** | 92 | 128 |
| 9C | 5.73** | 92 | 103 |
| 2C | 7.18** | 94 | 148 |

*regarded as normal,
**elevated triglycerides value

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for purification of a nucleic acid comprising the steps of:
    (a) adsorbing the nucleic acid onto a substrate by contacting the substrate with a composition comprising:
        (i) an aqueous buffer,
        (ii) one or more salts having a concentration of about 1 to 10 M,
        (iii) a water-miscible, non-acidic organic compound selected from the group consisting of acetylacetone, dimethylsulfoxide, methylethylketone, methylpropylketone, isobutylmethylketone, gamma-butyrolactone, gamma-valerolactone, propylene carbonate, and N-methyl-2-pyrrolidone, and
        (iv) the nucleic acid;
    (b) contacting the substrate from step (a) with a solution comprising one or more salts having a concentration less than the concentration in step (a), thereby desorbing the nucleic acid from the substrate; and
    (c) separating the solution containing the desorbed nucleic acid from the substrate, thereby purifying the nucleic acid.

2. The method of claim 1 wherein the organic compound has a concentration of 1 to 50 percent by volume.

3. The method of claim 1 wherein the organic compound has a concentration of 3 to 30 percent volume by volume.

4. The method of claim 1 wherein the salts are selected from the group consisting of lithium chloride, sodium chloride, potassium chloride, sodium acetate, and urea.

5. The method of claim 1 wherein the salts are chaotropic salts selected from the group consisting of sodium perchlorate, guanidine hydrochloride, guanidine thiocyanate, guanidine isothiocyanate, and sodium iodide having a concentration of 1 to 8 M.

6. The method of claim 1 wherein the substrate comprises a porous or non-porous mineral substrate selected from the group consisting of silica gel, glass fibers, quartz fibers, and zeolites.

7. The method of claim 1 wherein the substrate comprises magnetically attractable particles coated with glass.

8. The method of claim 1 wherein, prior to the contacting step (b), the substrate with adsorbed nucleic acid is washed with a washing solution.

9. The method of claim 8 wherein the washing solution comprises the organic compound.

10. The method of claim 8 wherein the washing solution comprises between 1 and 100 percent by volume of the organic compound.

11. A method for adsorbing a nucleic acid onto a substrate comprising contacting the substrate with an aqueous solution comprising the nucleic acid and one or more salts having a concentration of 1 to 10 M and an organic compound selected from the group consisting of acetylacetone, dimethylsulfoxide, methylethylketone, methylpropylketone, isobutylmethylketone, gamma-butyrolactone, gamma-valerolactone, propylene carbonate, and N-methyl-2-pyrrolidone whereby the nucleic acid is adsorbed onto the substrate.

12. The method of claim 11 wherein the organic compound has a concentration of 1 to 50 percent by volume.

13. The method of claim 11 wherein the organic compound has a concentration of 3 to 30 percent by volume.

14. The method of claim 11 wherein the salts are selected from the group consisting of lithium chloride, sodium chloride, potassium chloride, sodium acetate, and urea.

15. The method of claim 11 wherein the salts are chaotropic salts selected from the group consisting of sodium perchlorate, guanidine hydrochloride, guanidine thiocyanate, guanidine isothiocyanate, and sodium iodide and the concentration is 1 to 8 M.

16. The method of claim 11 wherein the substrate comprises a porous or non-porous mineral substrate selected from the group consisting of silica gel, glass fibers, quartz fibers, and zeolites.

17. The method of claim 11 wherein the substrate comprises magnetically attractable particles coated with glass.

18. A method for adsorbing a nucleic acid onto a substrate comprising the steps of:
(a) providing an aqueous solution comprising the nucleic acid and one or more salts having a concentration of 1 to 10 M;
(b) providing the substrate in the form of powdered material;
(c) providing an organic compound selected from the group consisting of acetylacetone, dimethylsulfoxide, methylethylketone, methylpropylketone, isobutylmethylketone, gamma-butyrolactone, gamma-valerolactone, propylene carbonate, and N-methyl-2-pyrrolidone;
(d) dispersing the substrate in the organic compound to form a suspension of the substrate; and
(e) mixing the aqueous solution with the suspension whereby the nucleic acid is adsorbed onto the substrate.

19. The method of claim 18 wherein the organic compound has a concentration in the mixture of step (e) of 1 to 50 percent by volume.

20. The method of claim 18 wherein the organic compound has a concentration in the mixture of step (e) of 3 to 30 percent by volume.

21. The method of claim 18 wherein the salts are selected from the group consisting of lithium chloride, sodium chloride, potassium chloride, sodium acetate, and urea.

22. The method of claim 18 wherein the salts are chaotropic salts selected from the group consisting of sodium perchlorate, guanidine hydrochloride, guanidine thiocyanate, guanidine isothiocyanate, and sodium iodide and the concentration is 1 to 8 M.

23. The method of claim 18 wherein the substrate comprises a porous or non-porous mineral substrate selected from the group consisting of silica gel, glass, quartz, and zeolites.

24. The method of claim 18 wherein the substrate comprises magnetically attractable particles coated with glass.

25. A suspension comprising magnetically attractable particles coated with glass dispersed in an organic compound selected from the group consisting of acetylacetone, dimethylsulfoxide, methylethylketone, methylpropylketone, isobutylmethylketone, gamma-butyrolactone, gamma-valerolactone, propylene carbonate, and N-methyl-2-pyrrolidone.

26. A kit of parts for purifying a nucleic acid comprising:
(a) a solution comprising a buffer salt and a chaotropic salt selected from the group consisting of sodium perchlorate, guanidine hydrochloride, guanidine thiocyanate, guanidine isothiocyanate, and sodium iodide;
(b) an organic compound selected from the group consisting of acetylacetone, dimethylsulfoxide, methylethylketone, methylpropylketone, isobutylmethylketone, gamma-butyrolactone, gamma-valerolactone, propylene carbonate, and N-methyl-2-pyrrolidone;
(c) a buffer solution; and
(d) chromatographic and filtering material.

27. A kit of parts for purifying a nucleic acid comprising:
(a) a solution comprising a buffer salt and one or more salts selected from the group consisting of lithium chloride, sodium chloride, potassium chloride, sodium acetate, and urea;
(b) an organic compound selected from the group consisting of acetylacetone, dimethylsulfoxide, methylethylketone, methylpropylketone, isobutylmethylketone, gamma-butyrolactone, gamma-valerolactone, propylene carbonate, and N-methyl-2-pyrrolidone;
(c) a buffer solution; and
(d) chromatographic and filtering material.

28. A kit of parts for purifying a nucleic acid comprising:
(a) a solution comprising a buffer salt and a chaotropic salt selected from the group consisting of sodium perchlorate, guanidine hydrochloride, guanidine thiocyanate, guanidine isothiocyanate, and sodium iodide;
(b) a suspension according to claim 25; and
(c) a buffer solution.

29. A kit of parts for purifying a nucleic acid comprising:
(a) a solution comprising a buffer salt and a salt selected from the group consisting of lithium chloride, sodium chloride, potassium chloride, sodium acetate, and urea;
(b) a suspension according to claim 25; and
(c) a buffer solution.

30. A method for determining the presence of a nucleic acid in a biological sample comprising the steps of:
(a) lysing the biological sample to form a lysate comprising the nucleic acid;
(b) forming a composition comprising
   (i) the lysate,
   (ii) an aqueous buffer,
   (iii) one or more salts having concentration of 1 to 10 M,
   (iv) a water-miscible, non-acidic organic compound selected from the group consisting of acetylacetone, dimethylsulfoxide, methylethylketone, methylpropylketone, isobutylmethylketone, gamma-butyrolactone, gamma-valerolactone, propylene carbonate, and N-methly-2-pyrrolidone;
(c) contacting the composition with a substrate whereby the nucleic acid is adsorbed onto the substrate;
(d) contacting the substrate from step (c) with a solution comprising one or more salts having a concentration less than the concentration in step (b), thereby desorbing the nucleic acid from the substrate; and
(e) separating the solution containing the desorbed nucleic acid from the substrate; and
(f) detecting the presence of the nucleic acid in the solution from step (e), thereby determining the presence of the nucleic acid in the biological sample.

31. The method of claim 30 wherein the nucleic acid is RNA or DNA.

32. The method of claim 30 wherein the nucleic acid is RNA and the detecting step (f) comprises reverse transcription of the RNA to form a cDNA, amplification of the cDNA by PCR, and detection of the presence of the cDNA as a determination of the presence of the nucleic acid.

* * * * *